US007575916B2

(12) United States Patent
Carroll et al.

(10) Patent No.: US 7,575,916 B2
(45) Date of Patent: Aug. 18, 2009

(54) NUCLEIC ACID MOLECULE ENCODING A MHC CLASS I PEPTIDE EPITOPE FROM THE HUMAN 5T4 TUMOR-ASSOCIATED ANTIGEN AND VECTOR COMPRISING THE NUCLEIC ACID MOLECULE

(75) Inventors: Miles Carroll, Oxford (GB); Susan Kingsman, Oxford (GB); Irina Redchenko, Oxford (GB)

(73) Assignee: Oxford Biomedica (UK) Limited, Oxford (GB)

( * ) Notice: Subject to any disclaimer, the term of this patent is extended or adjusted under 35 U.S.C. 154(b) by 644 days.

(21) Appl. No.: 10/504,602

(22) PCT Filed: Feb. 13, 2003

(86) PCT No.: PCT/GB03/00670

§ 371 (c)(1),
(2), (4) Date: Aug. 12, 2004

(87) PCT Pub. No.: WO03/068816

PCT Pub. Date: Aug. 21, 2003

(65) Prior Publication Data

US 2005/0123918 A1 Jun. 9, 2005

(30) Foreign Application Priority Data

Feb. 13, 2002 (GB) ................. 0203419.7

(51) Int. Cl.
*C12N 1/00* (2006.01)
*C07H 21/02* (2006.01)
*C07H 21/04* (2006.01)
*A61K 38/00* (2006.01)
*A61K 38/08* (2006.01)

(52) U.S. Cl. ................... 435/320.1; 536/23.1; 536/23.5
(58) Field of Classification Search ........................ None
See application file for complete search history.

(56) References Cited

U.S. PATENT DOCUMENTS

| 4,558,035 | A | 12/1985 | Johnson |
| 5,118,672 | A | 6/1992 | Schinazi et al. |
| 5,356,779 | A | 10/1994 | Mozes et al. |
| 5,869,053 | A | 2/1999 | Stern et al. |

FOREIGN PATENT DOCUMENTS

| EP | 0110385 A2 | 6/1984 |
| EP | 0198328 A2 | 10/1986 |
| EP | 1152060 A1 | 11/2001 |
| GB | 2370571 A | 7/2002 |
| WO | WO89/07947 A1 | 9/1989 |
| WO | WO92/03568 A1 | 3/1992 |
| WO | WO97/19183 A2 | 5/1997 |
| WO | WO99/15683 A1 | 4/1999 |
| WO | WO99/15684 A2 | 4/1999 |
| WO | WO 00/29428 A2 | 5/2000 |
| WO | WO 01/00225 A1 | 1/2001 |
| WO | WO 02/38612 A2 | 5/2002 |

OTHER PUBLICATIONS

Myers, Kevin A., et al. "Isolation of a cDNA Encoding 5T4 Oncofetal Trophoblast Glycoprotein", *The Journal of Biological Chemistry*, (1994) 269(12):9319-9324.
Guschlbauer, et al. "Poly-2'-deoxy-2'-fluoro-cytidylic acid: enzymatic synthesis, spectroscopic characterization and interaction with poly-inosinic acid", *Nucleic Acids Res.* (1977) 4:1933.
Schibahara, et al. "Site-directed cleavage of RNA", *Nucleic Acids Res.* (1987) 15:4403.
Gershon, et al. "The nucleotide sequence around the capripoxvirus thymidine kinase gene reveals a gene shared specifically with leporipoxvirus", *J. Gen. Virol*, (1989) 70:525.
Weir, et al. "Nucleotide sequence of the vaccinia virus thymidine kinase gene and the nature of spontaneous frameshift mutations", *J. Virol.* (1983) 46:530.
Esposito, et al. "Nucleotide sequence of the thymidine kinase gene region of monkeypox and variola viruses", *Virology* (1984) 135:561.
Kilpatrick, et al. "Cloning and physical mapping of yada monkey tumor virus DNA" *Virology* (1985) 143:399.
Binns, et al. "Comparison of a conserved region in fowlpox virus and vaccinia virus gnomes and the translocation of the fowlpox virus thymidine kinase gene", *J. Gen Virol* (1988) 69:1275.
Schnitzlein, et al. "A rapid method for identifying the thymidine kinase genes of avipoxviruses", *J. Virological Method* (1988) 23:341.
Fathi, et al. "Efficient targeted insertion of an unselected marker into the vaccinia virus genome", *Virology* (1986) 97:105.
Graham, et al. "A new technique for the assay of infectivity of human adenovirus 5 DNA", *Virol.* (1973) 52:456-467.
Straubinger, et al. "Liposomes as carriers for intracellular delivery of nucleic acids", *Methods in Enzymology*, (1983) 101:512-527.
Studier, et al. "Use of T7 RNA polymerase to direct expression of cloned genes", *Methods in Enzymol.* (1990) 185:60-89.

(Continued)

*Primary Examiner*—G. R Ewoldt
*Assistant Examiner*—DiBrino Marianne
(74) *Attorney, Agent, or Firm*—Marshall, Gerstein & Borun LLP

(57) ABSTRACT

There is provided an MHC class I peptide epitope from 5T4 antigen. In particular, there is provided a peptide epitope of 5T4 which comprises one of the following: (i) the amino acid sequence shown as SEQ ID No. 2; (ii) the minimal epitope from the amino acid sequence shown as SEQ ID No. 3; (iii) the minimal epitope from the amino acid sequence shown as SEQ ID No. 4. (iv) the minimal epitope from the amino acid sequence shown as SEQ ID No. 5. (v) the minimal epitope from the amino acid sequence shown as SEQ ID No. 6. (vi) the minimal epitope from the amino acid sequence shown as SEQ ID No. 7. There is also provided a vaccine comprising such a peptide (or precursor thereof) and its use to treat and/or prevent a disease, in particular a cancerous disease. There is also provided a nucleic acid molecule encoding a MHC class I peptide epitope from the human 5T4 tumor-associated antigen and vector comprising the nucleic acid molecule.

2 Claims, 10 Drawing Sheets

OTHER PUBLICATIONS

Matthias, et al. "Eukaryotic expression vectors for the analysis of mutant proteins", *NAR* (1989) 17:6418.

Wootton & Federhen, "Statistics of local complexity in amino acid sequences and sequence databases", *Computers and Chemistry* (1993) 17:149-163.

Myers, et al. "Isolation of a cDNA encoding 5T4 oncofetal trophoblast glycoprotein", *J. Biol. Chem.* (1994) 169:9319-9324.

Starzynska, et al. "The expression of 5T4 antigen in colorectal and gastic carcinoma", *Br. J. Cancer* (1992) 66(5):867-869.

Starzynska, et al. "Prognostic signficance of 5T4 oncofetal antigen expression in colorectal" *Br. J. Cancer* (1994) 69(5):899-902.

Hobbs, et al. "Polynucleotides containing 2'-amino-2'-deoxyribose and 2'-azido-2'-deoxyribose", *Biochemistry* (1973) 12:5138.

Starzynska, et al. "5T4 oncofetal antigen in gastric carcinoma and its clinical significance", *Eur J. Gastroenterol Hepatol* (1998) 10(6)479-484.

Carsberg, et al. "Metastasis-associated 5T4 antigen disrupts cell-cell contacts and induces cellular motility in epithelial cells", *Int. J. Cancer* (1996) 68(1):84-92.

Yewdell, et al. "TAP-independent delivery of antigenic peptides to the endoplasmic reticulum: therapeutic potential and insights into TAP-dependent antigen processing", *J. Immunotherapy* (1998) 21:127-31.

Carroll, et al. "Construction and characterization of a triple-recombinant vaccinia virus encoding B7-1, interleukin 12, and a model tumor antigen", *J. Natl. Cancer Inst.* (1998) 90(24):1881-1887.

Carroll, et al. "Two bright new faces in gene therapy", *Nature Biotechnology* (1996) 14:556.

Pieken, et al. "Kinetic characterization of ribonuclease-resistant 2'-modified hammerhead ribozymes", *Science* (1991) 253:314-317.

Parker, et al. "Scheme for ranking potential HLA-A2 binding peptides based on independent binding of individual peptide sidechains", *J. Immunol.* (1994) 152:163-175.

Fu, et al. "An endoplasmic reticulum-targeting signal sequence enhances the immunogenicity of an immunorecessive simian virus 40 large T antigen cytotoxic T-lymphocyte epitope", *J. Virol.* (1998) 72:1469-81.

Schödel, et al. "Hepatitis B virus core and e antigen: immune recognition and use as a vaccine carrier moiety", *Intervirology* (1996) 39:104-10.

Wolff and Trubetskoy "The cambrian period of nonviral gene delivery", *Nature Biotechnology* (1998), 16:421-423.

Taylor, et al. "Biological and immunogenic properties of a canarypox-rabies recombinant, ALVAC-RG (vCP65) in non-avian species", *Vaccine* (1995) 13:539-549.

Stannard, et al. "Evidence for incomplete replication of a penquin poxvirus in cells of mammalian origin", *J. Gen. Virol.* (1998) 79:1637-46.

Mackett, et al. "Vaccinia virus: a selectable eukaryotic cloning and expression vector", *PNAS* (1982) 79:7415-7419.

Upton, et al. "Identification and nucleotide sequence of the thymidine kinase gene of shope fibroma virus", *J. Virology* (1986) 60:920.

Boyle, et al. "Fowlpox virus thymidine kinase: nucleotide sequence and relationships to other thymidine kinase", *Virology* (1987) 156:355-365.

Lewis, et al. "Human immunodeficiency virus infection of cells arrested in the cell cycle" *EMBO J.* (1992) 11:3053-3058.

Lewis and Emerman, "Passage through mitosis is required for oncoretroviruses but not for the human immunodeficiency virus", *J. Virol.* (1994) 68:510-516.

Mackett, et al. "General method for production and selection of infectious vaccinia virus recombinants expressing foreign genes", *J. Virol.* (1984) 49:857-864.

Hruby, et al. "Fine structure analysis and nucleotide sequence of the vaccinia virus thymidine kinase gene", *PNAS*, (1983) 80:3411-3415.

Lytvyn, et al. "Comparison of the thymidine dinase genes from three entompoxiruses", *J. Gen Virol*, (1992) 73:3235-3240.

Smith, et al. "Vaccinia virus immune evasion", *Immuno Rev.* (1997) 159:137-154.

Jenkins, et al. "Formation of lentivirus particles by mammalian cells infected with recombinant fowlpox virus", *AIDS Research and Human Retroviruses* (1991) 7:991-998.

Taylor, et al. "Recombinant fowlpox virus inducing protective immunity in non-avian species", *Vaccine* (1988) 6:497-503.

Nakano, et al. "Molecular genetics of vaccinia virus: demonstration of marker rescue", *Proc. Natl. Acad. Sci. USA* (1982) 79:1593-1596.

Chakrabarti, et al. "Vaccinia virus expression vector: coexpression of β-galactosidase provices visual screening of recombinant virus plaques", *Mol. Cell. Biol.* (1985) 3403-3409.

Wigler, et al. "Transformation of mammalian cells with genes from prokaryotes and eukaryotes", *Cell*, (1979), 777-785.

Graessmann, et al. "Microinjection of tissue culture cells", *Meth. Enzymology* (1983) 101:482-492.

Franke, et al. "Neomycin resistance as a dominant selectable marker for selection and isolation of vaccinia virus recombinants", *Mol. Cell. Biol.* (1985) 1918-1924.

Altenburger, W., et al. "Partial deletion of the human host range gene in the attenuated vaccinia virus MVA" *Arch. Virol.* (1989) 105:15-27.

Neumann, et al. "Gene transfer into mouse lyoma cell by electroporation in high electric fields", *EMBO J.* (1982) 1:841-845.

Schaffner, "Direct transfer of cloned genes from bacteria to mammalian cells", *Proc. Natl. Acad. Sci. USA* (1980) 77:2163-2167.

Nestle, F.O., et al. Vaccination of melanoma patients with peptide-or tumor lysate-pulsed dendritic cells', *Nat. Med.* (1998) 4(3):328-32.

Altschul, et al. "Issues in searching molecular sequence database" *Nature Genetics* (1994) 6:119-129.

Carroll, et al. "Host range and cytopathogenicity of the highly attenuated MVA strain of vaccinia virus: propagation and generation of recombinant viruses in a nonhuman mammalian cell line", *Virology* (1997) 238:198-211.

Kim, C. J., et al. "Dendritic cell infected with poxviruses encoding Mart-1/melan a sensitive T lymphocytes in vitro", *J. Immunother* (1997) 20(4):276-86.

Schneider, et al. "Enhanced immunogenicity for CD8 + T cell induction and complete protective efficacy of malaria DNA vaccination by boosting with modified vaccinia virus Ankara", *Nat. Med.* (1998) 4:397-402.

Chakrabarti, et al. "Compact, synthetic, vaccinia virus early/late promoter for protein expression" *Biotechniques* (1997) 23:1094-1097.

Wyatt, et al. "Development of replication-deficient recombinant vaccinia virus vaccine effective against parainfluenza virus 3 infection in an animal model", *Vaccine* (1996) 14:1451-1458.

Sutter, et al. "A recombinant vector derived from the host rangerestricted and highly attenuated MVA strain of vaccinia virus stimulates protective immunity in mice to influenza virus", *Vaccine* (1994) 12:1032-1040.

Carroll, et al. "*E. coli* β-glucuronidase (GUS) as a marker for recombinant vaccinia viruses", *Biotechniques* (1995) 19:352-355.

Hirsch, et al. "Patterns of viral replication correlate with outcome in simian immunodeficiency virus (SIV)- infected macaques: effect of prior immunization with a trivalent SIV vaccine in modified vaccinia virus Ankara", *J. Virol.* (1996) 70:3741-3752.

Sutter, et al. "Nonreplicating vaccinia vector efficiently expresses recombinant genes", *Proc. Natl. Acad. Sci. USA*, (1992) 89:10847-10851.

Bronte, et al. "Antigen expression by dendritic cells correlates with the therapeutic effectiveness of a model recombinant poxvirus tumor vaccine", *Proc. Natl. Acad. Sci. USA* (1997) 94(7):3183-3188.

Wyatt, et al. "Replication-deficient vaccinia virus encoding bacteriophage T7 RNA polymerase for transient gene expression in mammalian cells", *Virology* (1995) 210:202-205.

Carroll, et al. "Highly attenuated modified vaccinia virus Ankara (MVA) as an effective recombinant vector: a Murine tumor model", *Vaccine* (1997) 15:387-394.

Sutter, et al. "Non-replication vaccinia vector efficiently expresses bacteriophage T7 RNA polymerase", *FEBS lett.* (1995) 371:9-12.

Overwijk, et al. "gp100/pmel 17 is a murine tumor rejection antigen induction of Self—reactive, tumoricidal T cells using high-affinity, altered peptide ligand", *J. Exp. Med.* (1998) 188:277-286.

Hole, N., et al. "Isolation and characterization of 5T4, a tumor-associated antigen", *Int. J. Cancer* (1990) 45(1):179-184.

Correale, Pierpaolo, et al. "Generation of Human Cytolytic T Lymphocyte Lines Directed Against Prostate-Specific Antigen (PSA) Employing a PSA Oligoepitope Peptide", *The Journal of Immunology* (1998) 161:3186-3194.

Hodge, James W., et al. "A Recombinant Vaccinia Virus Expressing Human Prostate-Specific Antigen (PSA): Safety and Immunogenicity in a Non-Human Primate", *Int. J. Cancer* (1995) 63:213-237.

Hole, N., et al. "A 72 kD trophoblast glycoprotein defined by a monoclonal antibody", *Br. J. Cancer* (1998) 57:239-246.

Irvine, Kari R., et al. "Synthetic Oligonucleotide Expressed by a Recombinant Vaccinia Virus Elicits Therapeutic CTL", *The Journal of Immunology* (1995) 154:4651-4657.

Jackson, Ronald J., et al. "Infertility in Mice Induced by a Recombinant Ectromelia Virus Expressing Mouse Zona Pellucida Glycoprotein 3", *Biology of Reproduction* (1998) 58:152-159.

Kass, Erik, et al. "Induction of Protective Host Immunity to Carcinoembryonic Antigen (CEA), a Self-Antigen in CEA Transgenic Mice, by Immunizing with a Recombinant Vaccinia-CEA Virus", *Cancer Research* (1999) 59:676-683.

Rosato, Antonio, et al. "CTL Response and Protection Against P815 Tumor Challenge in Mice Immunized with DNA Expressing the Tumor-Specific Antigen P815A", *Human Gene Therapy* (1997) 8:1451-1458.

Sanda, Martin G., et al. "Recombinant Vaccinia-PSA (Prostvac) Can Induce a Prostate-Specific Immune Response in Androgen-Modulated Human Prostate Cancer", *Urology* (1999) 53:260-266.

Southall, P.J., et al. "Immunohistological distribution of 5T4 antigen in normal and malignant tissues", *Br. J. Cancer* (1990) 61:89-95.

Tsang, Kwong Y., et al. "Generation of Human Cytotoxic T Cells Specific for Human Carcinoembryonic Antigen Epitopes From Patients Immunized With Recombinant Vaccinia-CEA Vaccine", *J. Natl. Cancer Inst.* (1995) 87(13):982-990.

Wang, Rong-Fu "Tumor Antigens Discovery: Perspectives for Cancer Therapy", *Molecular Medicine* (1997) 3(11):716-731.

Perkins, David L., et al. "Immunodominance: Intramolecular Competition Between T-Cell Epitopes", *J. Immunol.* (1997) 146(7):2137-2144.

Theobald, Matthias, et al. "The Sequence Alteration Associated with a Mutational Hotspot in p53 Protects Cells from Lysis by Cytotoxic T Lymphocytes Specific for a Flanking Peptide Epitope", *J. Exp. Med.* (1998) 188(6):1017-1028.

Gileadi, Uzi, et al. "Effect of epitope flanking residues on the presentation of N-terminal cytotoxic T lymphocyte epitopes", *Eur. J. Immunol.* (1999) 29:2213-2222.

Engelhard, Victor H. "Structure of peptides associated with MHC class 1 molecules", *Current Opinion in Immunology* (1994) 6:13-23.

Eisenlohr, Laurence C., et al. "Flanking Sequences Influence the Presentation of an Endogenously Synthesized Peptide to Cytotoxic T Lymphocytes", *J. Exp. Med.* (1992) 175:481-487.

Shastri, Nilbah, et al. "Presentation of Endogenous Peptide/MHC Class I Complexes is Profoundly Influenced by Specific C-Terminal Flanking Residues", *J. Immunol.* (1995) 155:4339-4346.

Bergmann, Cornelia C., et al. "Differential Effects of Flanking Residues on Presentation of Epitopes from Chimeric Peptides", *J. Virol.* (1994) 68(8):5306-5310.

Wang, Yusheng, et al. "Silencing of Immunodominant Epitopes by Contiguous Sequences in Complex Synthetic Peptides", *Cell Immunol.* (1992) 143:284-297.

Celis, Esteban, et al. "Identification of Potential CTL Epitopes of Tumor-Associated Antigen Mage-1 for Five Common HLA-A Alleles", *Molec.Immunol.* (1994) 31(18):1423-1430.

Guo, Hwai-Chen, et al. "Different length peptides bind to HLA-Aw68 similarity at their ends but bulge out in the middle", *Nature* (1992) 360:364-366.

Ochoa-Garay, Jorge, et al. "The Ability of Peptides to Induce Cytotoxic T Cells In Vitro Does Not Strongly Correlate With Their Affinity for H-2L$^d$ Molecule: Implications for Vaccine Design and Immunotherapy", *Molec. Immunol.* (1997) 34(3):273-281.

Chaux, Pascal, et al. "Estimation of the Frequencies of Anti-Mage-3 Cytolytic T-Lymphocyte Precursors in Blood From Individuals Without Cancer", *Int. J. Cancer* (1998) 77:538-542.

GenEmbl Accession No. Z29083 (1998).

Stern, Peter, et al. "Characterization of the Human Trophoblast-Leukocyte Antigenic Molecules Defined by a Monoclonal Antibody", *The Journal of Immunology* (1986) 137(5):1604-1609, Abstract.

Johnson, P.M., et al. Human Trophoblast-Specific Surface Antigens Identified Using Monoclonal Antibodies', *American Journal of Reproductive Immunology* (1981) 1:246-254.

Rettig, Wolfgang J., et al. "Cell Surface Antigens of Human Trophoblast and Choriocarcinoma Defined by Monoclonal Antibodies", *Int. J. Cancer* (1985) 35:469-475.

Hole, M., et al. "Trophoblast-Specific Glycoprotein Defied by Monoclonal Antibody 5T4", *British Society for Immunology & British Transplantation Society 1986 Joint Annual Meeting*. Nov. 12-14, 1986, abstract 66.

Anderson, Deborah J., et al. Monoclonal antibodies to human trophoblast and sperm antigens: Report of two WHO sponsored workshops, Jun. 30, 1986—Toronto, Canada *J. Repro. Immun.* (1987) 10:231-257.

Cho, S.-W.,et al. "Characterization of three monoclonal antibodies to membrane co-factor protein (MCP) of the complement system and quantification of MCP by radioassay", *Clin. Exp. Immunol.* (1991) 83:257-261.

Purcell, D.F.J., et al. "The human cell-surface glycoproteins HuLym5, membrane co-factor protein (MCP) of the complement system, and trophoblast leucocyte-common (TLX) antigen, are CD46", *Immunology* (1990) 70:155-161.

Coulie P. "Human Tumor Antigens Recognized by Cytolytic T Lymphocyes", Chapter 5, pp. 95-125, *Tumor Immunology*, Eds. Dagleish & Browning, Cambridge University Press 1996.

Rosenkrantz, K., et al. "Generation and regulation of autocytotoxicity in mixed lymphocyte cultures: Evidence for active suppression of autocytotoxic cells", *PNAS* (1985) 82:4508-4512.

Stavely-O'Carroll, et al. "Induction of antigen-specific T cell energy: An early event in the course of tumor progression", *PNAS* (1998) 95:1178-1183.

Manson, L, et al. "Short Analytical Review—Anti-tumor Immune Responses of the Tumor Bearing Host: The Case for Antibody-Mediated Immunologic Enhancement", *Clinical Immunology & Immunopathology* (1994) 72(1):1-8.

Ganss, R., et al. "Tumor Microenvironment Can Restrict the Effectiveness of Activated Antitumor Lymphocytes", *Cancer Research* (1998) 58:4673-4681.

Berd, D. "Cancer Vaccines: Reborn or Just Recycled?", *Seminars in Oncology* (1998) 25(6):605-610.

Hersey, P., et al. "Impediments to Successful Immunotherapy", *Pharmacol. Ther.* (1999) 81(2):111-119.

Takahashi, K., et al. "Escape Mechanisms of Melanoma From Immune System By Soluble Melanoma Antigen", *The Journal of Immunology* (1988) 140(9):3244-3248.

Janeway & Travers, *Immunobiology: The Immune System in Health and Disease*, Third edition, Current Biology Ltd./Garland Publishing Inc. (1997), p. 12:2.

Amato, R., et al. Phase II Trial to Assess the Activity of MVA 5T4 (Trovax®) alone versus MVA 5T4 plus Granulocyte Macrophage Colony-Stimulating Factor (GM-CSF) in Patients (pts) with Progressive Hormone Refractory Prostate Cancer (HRPC), Abstract, 18th EORTC-NCI-AACR Symposium on "Molecular Targets and Cancer Therapeutics", Nov. 7-10, 2006, Prague, Czech Republic.

Amato, R., et al. Activity of MVA 5T4 alone or in Combination with either Interleukin-2 (IL-2), Interferon-α (IFN), or Sunitinib in Patients (Pts) with Metastatic Renal Cell Cancer (MRCC), Abstract, 18th EORTC-NCI-AACR Symposium on "Molecular Targets and Cancer Therapeutics", Nov. 7-10, 2006, Prague, Czech Republic.

Sykulev, Y., et al. "Evidence that a Single Peptide-MHC Complex on a Target Cell Can Elicit a Cytolytic T Cell Response", *Immunity* (1996) 4:565-571.

Calvert et al. "Fowlpox virus recombinants expressing the envelope glycoprotein of an avian reticuloendotheliosis retrovirus induce neutralizing antibodies and reduce viremia in chickens," *J. Virol.* (1993) 67:3069-3076.

Boursnell et al. "Insertion of the fusion gene from Newcastle disease virus into a non-essential region in the terminal repeats of fowlpox virus and demonstration of protective immunity induced by the recombinant," *J. Gen. Virol.* (1990) 71:621-628.

Stern et al., "Molecular characterization of human terato-carcinoma-trophoblast cell surface antigens," *J. Repro. Immun.*, (Jun. 1986) Supp: 6.

Office Action, U.S. Appl. No. 10/504,603, United States Patent and Trademark Office, mailed Sep. 11, 2007, VanderVegt.

IFN-γ production by OB8 T cell clones

| Stimulation | CONTROLS (background) | | | | | EXPERIMENT | | |
|---|---|---|---|---|---|---|---|---|
| | T cells | LCL | T cells + LCL | T cells + MVA-LacZ | | T cells + LCL | | |
| Clone No. | | | | | | TroVax | p77 | |
| Cytolytic | | | | | | | | |
| 47 | - | - | +++ | +++ | | ++++ | +++ | |
| 77 | - | - | ++ | ++ | | +++ | ++ | |
| Non-Cytolytic | | | | | | | | |
| 30 | - | - | ++ | ++ | | +++ | +++ | |
| 32 | - | - | - | - | | + | - | |
| 37 | - | - | - | - | | + | + | |
| 43 | - | - | ++ | ++ | | +++ | +++ | |
| 44 | - | - | ++ | ++ | | ++ | ++ | |

FIG. 5

| Target cells | Auto LCL | Auto LCL+ | Auto LCL+ | Auto LCL+ | Auto LCL+ | Auto LCL+ | Auto LCL+ | Auto LCL+ | Auto LCL+ |
|---|---|---|---|---|---|---|---|---|---|
| | | p77 | c1 | c2 | c3 | c4 | c5 | c6 | c7 | c8 |
| Spont /Max | 81/ 1209 | 95/ 1127 | 76/ 1089 | 86/ 1152 | 97/ 1182 | 94/ 1194 | 68/ 1077 | 80/ 1063 | 79/ 1145 | 86/ 942 |
| Clone No. | | | | | | | | | | |
| 14 | 73 | 69 | 76 | 70 | 74 | 73 | 78 | 72 | 73 | 76 |
| 15 | 10 | 9 | 10 | 6 | 12 | 8 | 27 | 12 | 10 | 10 |
| 21 | 9 | 8 | 9 | 7 | 10 | 6 | 8 | 11 | 8 | 10 |
| 32 | 22 | 21 | 21 | 22 | 22 | 21 | 23 | 22 | 22 | 23 |
| 95 | 44 | 41 | 44 | 37 | 43 | 39 | 45 | 44 | 46 | 50 |
| 40 | 32 | 30 | 32 | 25 | 28 | 26 | 32 | 33 | 32 | 34 | c1  NPLADLSPFAFS
c2  NPLADLSPFAF
c3  PLADLSPFAFS
c4=p77  PLADLSPFAF
c5  PLADLSPFA
c6  PLADLSPF
c7  LADLSPFAF
c8  ADLSPFAF

OB8 CTL assay

| Target cells | % specific lysis |
|---|---|
| Auto LCL cont. | 17% |
| Auto LCL + peptide | 67% |
| GS LCL cont. | 11% |
| GS LCL + peptide | 36% |
| IM17 LCL cont. | 16% |
| IM17 LCL + peptide | 18% |

Amino acid sequence of positive 5T4 peptides 14.2 LHLEDNALKV 14.3 LEDNALKVLH

Amino acid sequence of the shorter
versions of 14.3 and 14.2 peptides

3 HLEDNALKV

10 LEDNALKVL

11 LEDNALKV

SEQUENCE LISTING

<160> NUMBER OF SEQ ID NOS: 15

<210> SEQ ID NO 1
<211> LENGTH: 1260
<212> TYPE: DNA
<213> ORGANISM: Felis catus

<400> SEQUENCE: 1

```
atgcctgggg ggtgctcccg gggccccgcc gccggagacg ggcggctgcg gctggcgcgg      60
ctggcgctgg tcctcctggg ctgggtctct tcgtcttctc tcacttcctc ggcgccctcc     120
```

-continued

```
acctcctcca cgtcgttcct ggcctccgcg gtgtccgccc agccccgct gccgggccaa      180 tgccccagc tttgcgagtg ctccgaggcg gcgcgcactg tcaagtgcgt taaccgcaac      240
ctgaccgagg tgcccgcgga cctgccccc tacgtgcgca acctcttcct caccggcaat     300
cagctggccg tgctccccgc cggcgccttc gcccgccggc cgccgctggc ggagctggcc    360
gcgctcaacc tcagcggcag ccgcctgcag gaggtgcgcg ccggcgcctt cgagcaactg    420
cccagcctgc ggcagctcga cctcagccac aacccgctgg cccacctcag ccccttcacc    480
ttctcgggca gcaacgccag cttctcggcc ccagccccc tggtggaact gatgctgaac     540
cacatcgtgc cccctgagga ccaccggcac aaccggagct cgagggtat ggtggcggcg     600 tccctacgcg ccggccatgc gcttcgcggg ctccagcgcc tygaactggc cagcaaccac    660
ttcctcttct tgcctcggga cgtactggcc cacctaccgg gcctcaggca cctgacctg    720 cgcaacaact cgctggtgag cctaacttac gtgtccttcc gcaacctgac acacctacaa    780
agcctccacc tggaggacaa cgccctcaag gtccttcaca cggcaccat ggcggagttg     840 cagagcctgc cccacgtcag ggtcttcctg gacaacaatc cctgggtctg cgactgtcac    900
atggtggaca tggtggcctg gctcaaggag acagaggtag tgcagggcaa agccaggctc    960
gcctgtgcat tcccggaaaa aatgaggaat cgggcccttt tggaactcaa cagctcccac   1020
ctggagtgtg accctatcct ccctccatcc ctgcagactt cttatgtctt tctaggtatt   1080
gttttagccc tgataggtgc catttcta ctggttttgt acttgaaccg caaggggata    1140
aaaaagtgga tgcataacat cagagatgcc tgcagggatc acatggaagg gtatcactac  1200
agatatgaaa tcaacgcgga ccccaggtta acaaacctca gttctaattc ggatgtctga  1260
```

<210> SEQ ID NO 2
<211> LENGTH: 419
<212> TYPE: PRT
<213> ORGANISM: Felis catus
<220> FEATURE:
<221> NAME/KEY: MISC_FEATURE
<223> OTHER INFORMATION: Protein sequence of seq id No. 1

<400> SEQUENCE: 2

```
Met Pro Gly Gly Cys Ser Arg Gly Pro Ala Ala Gly Asp Gly Arg Leu
1               5                   10                  15

Arg Leu Ala Arg Leu Ala Leu Val Leu Leu Gly Trp Val Ser Ser Ser
            20                  25                  30

Ser Leu Thr Ser Ser Ala Pro Ser Thr Ser Ser Thr Ser Phe Leu Ala
        35                  40                  45

Ser Ala Val Ser Ala Gln Pro Pro Leu Pro Gly Gln Cys Pro Gln Leu
    50                  55                  60

Cys Glu Cys Ser Glu Ala Ala Arg Thr Val Lys Cys Val Asn Arg Asn
65                  70                  75                  80

Leu Thr Glu Val Pro Ala Asp Leu Pro Pro Tyr Val Arg Asn Leu Phe
                85                  90                  95

Leu Thr Gly Asn Gln Leu Ala Val Leu Pro Ala Gly Ala Phe Ala Arg
            100                 105                 110

Arg Pro Pro Leu Ala Glu Leu Ala Ala Leu Asn Leu Ser Gly Ser Arg
        115                 120                 125

Leu Gln Glu Val Arg Ala Gly Ala Phe Glu Gln Leu Pro Ser Leu Arg
    130                 135                 140

Gln Leu Asp Leu Ser His Asn Pro Leu Ala His Leu Ser Pro Phe Thr
145                 150                 155                 160
```

```
Phe Ser Gly Ser Asn Ala Ser Phe Ser Ala Pro Ser Pro Leu Val Glu
                165                 170                 175

Leu Met Leu Asn His Ile Val Pro Pro Glu Asp His Arg His Asn Arg
            180                 185                 190

Ser Phe Glu Gly Met Val Ala Ala Ser Leu Arg Ala Gly His Ala Leu
        195                 200                 205

Arg Gly Leu Gln Arg Leu Glu Leu Ala Ser Asn His Phe Leu Phe Leu
    210                 215                 220

Pro Arg Asp Val Leu Ala His Leu Pro Gly Leu Arg His Leu Asp Leu
225                 230                 235                 240

Arg Asn Asn Ser Leu Val Ser Leu Thr Tyr Val Ser Phe Arg Asn Leu
                245                 250                 255

Thr His Leu Gln Ser Leu His Leu Glu Asp Asn Ala Leu Lys Val Leu
            260                 265                 270

His Asn Gly Thr Met Ala Glu Leu Gln Ser Leu Pro His Val Arg Val
        275                 280                 285

Phe Leu Asp Asn Asn Pro Trp Val Cys Asp Cys His Met Val Asp Met
    290                 295                 300

Val Ala Trp Leu Lys Glu Thr Glu Val Val Gln Gly Lys Ala Arg Leu
305                 310                 315                 320

Ala Cys Ala Phe Pro Glu Lys Met Arg Asn Arg Ala Leu Leu Glu Leu
                325                 330                 335

Asn Ser Ser His Leu Glu Cys Asp Pro Ile Leu Pro Pro Ser Leu Gln
            340                 345                 350

Thr Ser Tyr Val Phe Leu Gly Ile Val Leu Ala Leu Ile Gly Ala Ile
        355                 360                 365

Phe Leu Leu Val Leu Tyr Leu Asn Arg Lys Gly Ile Lys Lys Trp Met
    370                 375                 380

His Asn Ile Arg Asp Ala Cys Arg Asp His Met Glu Gly Tyr His Tyr
385                 390                 395                 400

Arg Tyr Glu Ile Asn Ala Asp Pro Arg Leu Thr Asn Leu Ser Ser Asn
                405                 410                 415

Ser Asp Val

<210> SEQ ID NO 3
<211> LENGTH: 9
<212> TYPE: PRT
<213> ORGANISM: Artificial sequence
<220> FEATURE:
<223> OTHER INFORMATION: Protein fragment

<400> SEQUENCE: 3

Pro Leu Ala Asp Leu Ser Pro Phe Ala
1               5

<210> SEQ ID NO 4
<211> LENGTH: 10
<212> TYPE: PRT
<213> ORGANISM: Artificial sequence
<220> FEATURE:
<223> OTHER INFORMATION: Protein fragment

<400> SEQUENCE: 4

Leu His Leu Glu Asp Asn Ala Leu Lys Val
1               5                   10
```

```
<210> SEQ ID NO 5
<211> LENGTH: 10
<212> TYPE: PRT
<213> ORGANISM: Artificial sequence
<220> FEATURE:
<223> OTHER INFORMATION: Protein fragment

<400> SEQUENCE: 5

Leu Glu Asp Asn Ala Leu Lys Val Leu His
1               5                   10

<210> SEQ ID NO 6
<211> LENGTH: 9
<212> TYPE: PRT
<213> ORGANISM: Artificial sequence
<220> FEATURE:
<223> OTHER INFORMATION: protein fragment

<400> SEQUENCE: 6

His Leu Glu Asp Asn Ala Leu Lys Val
1               5

<210> SEQ ID NO 7
<211> LENGTH: 9
<212> TYPE: PRT
<213> ORGANISM: Artificial sequence
<220> FEATURE:
<223> OTHER INFORMATION: protein fragment

<400> SEQUENCE: 7

Leu Glu Asp Asn Ala Leu Lys Val Leu
1               5

<210> SEQ ID NO 8
<211> LENGTH: 8
<212> TYPE: PRT
<213> ORGANISM: Artificial sequence
<220> FEATURE:
<223> OTHER INFORMATION: Protein fragment

<400> SEQUENCE: 8

Leu Glu Asp Asn Ala Leu Lys Val
1               5

<210> SEQ ID NO 9
<211> LENGTH: 12
<212> TYPE: PRT
<213> ORGANISM: Artificial sequence
<220> FEATURE:
<223> OTHER INFORMATION: protein fragment c1 from fig. 6

<400> SEQUENCE: 9

Asn Pro Leu Ala Asp Leu Ser Pro Phe Ala Phe Ser
1               5                   10

<210> SEQ ID NO 10
<211> LENGTH: 11
<212> TYPE: PRT
<213> ORGANISM: Artificial sequence
<220> FEATURE:
<223> OTHER INFORMATION: sequence fragment c2 from fig. 6

<400> SEQUENCE: 10

Asn Pro Leu Ala Asp Leu Ser Pro Phe Ala Phe
1               5                   10
```

```
<210> SEQ ID NO 11
<211> LENGTH: 11
<212> TYPE: PRT
<213> ORGANISM: Artificial sequence
<220> FEATURE:
<223> OTHER INFORMATION: Protein fragment c3 from fig. 6

<400> SEQUENCE: 11

Pro Leu Ala Asp Leu Ser Pro Phe Ala Phe Ser
1               5                   10

<210> SEQ ID NO 12
<211> LENGTH: 10
<212> TYPE: PRT
<213> ORGANISM: Artificial sequence
<220> FEATURE:
<223> OTHER INFORMATION: Protein fragment c4 from fig. 6

<400> SEQUENCE: 12

Pro Leu Ala Asp Leu Ser Pro Phe Ala Phe
1               5                   10

<210> SEQ ID NO 13
<211> LENGTH: 8
<212> TYPE: PRT
<213> ORGANISM: Artificial sequence
<220> FEATURE:
<223> OTHER INFORMATION: Protein fragment C6 from fig. 6

<400> SEQUENCE: 13

Pro Leu Ala Asp Leu Ser Pro Phe
1               5

<210> SEQ ID NO 14
<211> LENGTH: 9
<212> TYPE: PRT
<213> ORGANISM: Artificial sequence
<220> FEATURE:
<223> OTHER INFORMATION: Protein fragment c7 from fig. 6

<400> SEQUENCE: 14

Leu Ala Asp Leu Ser Pro Phe Ala Phe
1               5

<210> SEQ ID NO 15
<211> LENGTH: 8
<212> TYPE: PRT
<213> ORGANISM: Artificial sequence
<220> FEATURE:
<223> OTHER INFORMATION: Protein fragment c8 from fig. 6

<400> SEQUENCE: 15

Ala Asp Leu Ser Pro Phe Ala Phe
1               5
```

NUCLEIC ACID MOLECULE ENCODING A MHC CLASS I PEPTIDE EPITOPE FROM THE HUMAN 5T4 TUMOR-ASSOCIATED ANTIGEN AND VECTOR COMPRISING THE NUCLEIC ACID MOLECULE

FIELD OF THE INVENTION

The present invention relates to peptide epitopes of 5T4 antigen, and their use in immunotherapy.

BACKGROUND OF THE INVENTION

Prior to the identification of specific human tumour antigens, many clinical trials were performed attempting to immunise cancer patients against either whole cancer cells or subcellular fractions from cancer cells. The identification of genes encoding tumour antigens, however, has made it possible to develop specific immunotherapies based on attacking tumour cells bearing the identified antigens. A variety of clinical approaches utilising these genes or gene products are possible as summarised in the following table.

---
Active immunotherapy ("Cancer vaccines")

1. Immunisation with:
   i) purified antigen
   ii) immunodominant peptide (native or modified)
   iii) "naked" DNA encoding the antigen
   iv) recombinant viruses encoding the antigen
   v) antigen presenting cells pulsed with protein or peptide (or transfected with genes encoding the antigen)
2. Use of cytokine adjuvants such as IL-2 and IL-12 administered systemically or encoded by the immunising vector Passive immunotherapy ("Adoptive immunotherapy")

1. Transfer of cells sensitized in vitro to the specific antigen (bulk or cloned populations)
2. Transduction of effector cells (or stem cells) with genes encoding T cell receptors that recognise sepcific antigens.
---

Immunisation with intact protein has the potential advantage of simultaneously immunising against both class I and class II epitopes but requires extensive and time-consuming efforts to purify large amounts of tumour antigen. The identification of class I and class II peptide within a tumour antigen makes it possible to immunise with high levels of pure synthetic peptide. The peptide approach also has the advantage that one can choose between a class I and a class II type response (or mixture) by choosing which epitopes to use. Immunisation with peptide also means that subdominant and/or cryptic epitopes can be chosen (as the need for antigen processing may be bypassed or reduced to a "trimming role) in order to stimulate a different subset of T cells. Also the peptide may be modified (for example at their HLA class I or II anchor sites) to increase their immunogenicity.

In the past few years, much attention has been given to the role of CD8+ T cells in tumour immunity. Tumour-specific CD8+ CTLs have been shown to be capable of lysing tumour cells directly and eradicating tumour masses in vivo in animal models. However, CD4+ T cells are also thought to play a critical role (Wang and Rosenberg (1999) Immunological Reviews 170:85-100) and it may be that optimal cancer vaccines require the participation of both CD4+ and CD8+ T cells.

A number of oncofoetal or tumour-associated antigens (TAAs) have been identified and characterised in human and animal tumours. In general, TAAs are antigens expressed during foetal development which are downregulated in adult cells, and are thus normally absent or present only at very low levels in adults. Tumour cells have been observed to resume expression of TAAs, and the application of TAAs for tumour diagnosis, targeting and immunotherapy has therefore been suggested.

The TAA 5T4 (see WO 89/07947) has been previously characterised. It is a 72kDa glycoprotein expressed widely in carcinomas, but having a highly restricted expression pattern in normal adult tissues (see Table 1). It appears to be strongly correlated to metastasis in colorectal and gastric cancer. The full nucleic acid sequence of human 5T4 is known (Myers et al., 1994 J Biol Chem 169: 9319-24).

TABLE 1

Distribution of Human 5T4

| Tumour Type | 5T4 Frequency (%) |
|---|---|
| Breast | 84 |
| Ovarian | 71 |
| Gastric | 74 |
| Colorectal | 85 |

(Starzynska et al., Eur J Gastroenterol Hepatol 1998 June; 10(6):479-84; Starzynska et al., Br J Cancer 1994 May;69(5): 899-902; Starzynska et al., Br J Cancer 1992 November;66 (5):867-9)

5T4 has been proposed as a marker, with possible mechanistic involvement, for tumour progression and metastasis potential (Carsberg et al., (1996) Int J Cancer 1996 Sep. 27;68(1):84-92). 5T4 has also been proposed for use as an immunotherapeutic agent (see WO 00/29428).

SUMMARY OF THE INVENTION

The present inventors have identified a number of MHC class I and II restricted epitopes of 5T4. The identification of particular antigenic peptides provides new opportunities for the development of diagnostic and therapeutic strategies against cancer.

Thus the first aspect of the present invention relates to MHC class I epitopes of 5T4 antigen. The invention provides peptide epitopes of 5T4 antigen which are capable of being presented in conjunction with an MHC class I molecule such that they are specifically recognised by a T cell.

In particular, the present invention provides a peptide epitope of 5T4 which comprises one of the following:
  (i) the amino acid sequence shown as SEQ ID No.2;
  (ii) the minimal epitope from the amino acid sequence shown as SEQ ID No.3;
  (iii) the minimal epitope from the amino acid sequence shown as SEQ ID No.4.
  (iv) the minimal epitope from the amino acid sequence shown as SEQ ID No.5.
  (v) the minimal epitope from the amino acid sequence shown as SEQ ID No.6.
  (vi) the minimal epitope from the amino acid sequence shown as SEQ ID No.7.

Further aspects of the invention relate to:
a polyepitope string comprising such a peptide.
such a peptide epitope, or such a polyepitope string in association with a cell penetrator.
such a peptide epitope, or such a polyepitope string associated with a tetramer.

a nucleic acid sequence capable of encoding such a peptide epitope or polyepitope string (and optionally an associated cell penetrator).

a vector system capable of delivering such a nucleic acid sequence to a cell.

a cell pulsed with such a peptide epitope (or a precursor thereof).

a vaccine comprising such a peptide epitope, a polyepitope string, nucleic acid sequence, vector system and/or cell.

the use of such a vaccine in the manufacture of a medicament for use in the prevention and/or treatment of a disease.

a method for treating and/or preventing a disease in a subject in need of same which comprises the step of administering an effective amount of such a vaccine to the subject.

an agent capable of binding specifically to such a peptide and/or nucleic acid sequence.

a method which comprises the step of detecting the presence of such a peptide, nucleic acid or agent in a subject.

a T cell line or clone capable of specifically recognising such a peptide epitope in conjunction with an MHC class I molecule.

Other aspects of the present invention are presented in the accompanying claims and in the following description and discussion. These aspects are presented under separate section headings. However, it is to be understood that the teachings under each section heading are not necessarily limited to that particular section heading.

DETAILED DESCRIPTION OF THE INVENTION

Epitopes

The present invention relates to peptide epitopes.

The term "peptide" is used in the normal sense to mean a series of residues, typically L-amino acids, connected one to the other typically by peptide bonds between the α-amino and carboxyl groups of adjacent amino acids. The term includes modified peptides and synthetic peptide analogues.

A T cell epitope is a short peptide derivable from a protein antigen. Antigen presenting cells can internalise antigen and process it into short fragments which are capable of binding MHC molecules. The specificity of peptide binding to the MHC depends on specific interactions between the peptide and the peptide-binding groove of the particular MHC molecule.

Peptides which bind to MHC class I molecules (and are recognised by CD8+ T cells) are usually between 6 and 12, more usually between 8 and 10 amino acids in length. The amino-terminal anine group of the peptide makes contact with an invariant site at one end of the peptide groove, and the carboxylate group at the carboxy terminus binds to an invariant site at the other end of the groove. The peptide lies in an extended confirmation along the groove with further contacts between main-chain atoms and conserved amino acid side chains that line the groove. Variations in peptide length are accommodated by a kinking in the peptide backbone, often at proline or glycine residues.

Peptides which bind to MHC class II molecules are usually at least 10 amino acids, for example about 13-18 amino acids in length, and can be much longer. These peptides lie in an extended confirmation along the MHC II peptide-binding groove which is open at both ends. The peptide is held in place mainly by main-chain atom contacts with conserved residues that line the peptide-binding groove.

The peptide of the present invention may be made using chemical methods (Peptide Chemistry, A practical Textbook. Mikos Bodansky, Springer-Verlag, Berlin.). For example, peptides can be synthesized by solid phase techniques (Roberge J Y et al (1995) Science 269: 202-204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage from a longer polypeptide. For example, the peptide may be obtained by cleavage from full-length 5T4. The composition of a peptide may be confirmed by amino acid analysis or sequencing (e.g., the Edman degradation procedure).

The term "peptide epitope" encompasses modified peptides. For example 5T4 peptides may be mutated, by amino acid insertion, deletion or substitution, so long as the MHC binding-specificity of the wild-type 5T4 peptide is retained. In a preferred embodiment the modified epitope has greater affinity for the peptide binding groove. Preferably the peptide contains 5 or fewer mutations from the wild-type sequence, more preferably 3 or fewer, most preferably 1 or 0 mutations.

Alternatively (or in addition) modifications may be made without changing the amino acid sequence of the peptide. For example, D-amino acids or other unnatural amino acids can be included, the normal amide bond can be replaced by ester or alkyl backbone bonds, N-or C-alkyl substituents, side chain modifications, and constraints such as disulphide bridges and side chain amide or ester linkages can be included. Such changes may result in greater in vivo stability of the peptide, and a longer biological lifetime.

Modification of epitopes may be performed based on predictions for more efficient T-cell induction derived using the program "Peptide Binding Predictions" devised by K. Parker (NIH) which may be found on the world wide web at bimas-.dcrt.nih.gov/cgi-bin/molbio/ken_parker_comboform (see also Parker, K. C et al. 1994. J.Immunol. 152:163).

A "modified" 5T4 peptide epitope includes peptides which have been bound or otherwise associated to transporter peptides or adjuvants, in order to increase their ability to elicit an immune response. For example, peptides may be fused to TAP independent transporter peptides for efficient transport to HLA and interaction with HLA molecules to enhance CTL epitopes (for review see Yewdell et al., 1998 J Immunother 21:127-31; Fu et al., (1998) J Virol 72:1469-81).

In a further embodiment, 5T4 or 5T4 peptides may be fused to hepatitis B core antigen to enhance T helper and antibody responses (Schodel et al., 1996 Intervirology 39:104-10).

To be an epitope, the peptide should be capable of binding to the peptide-binding groove of a MHC class I or II molecule and be recognised by a T cell.

Cell surface presentation of peptides derived from a given antigen is not random and tends to be dominated by a small number of frequently occurring epitopes. The dominance of a particular peptide will depend on many factors, such as relative affinity for binding the MHC molecule, spatio-temporal point of generation within the APC and resistance to degradation. The epitope hierarchy for an antigen is thought to change with progression of an immune response. After a primary immune response to the immunodominant peptides, epitope "spreading" may occur to sub-dominant determinants (Lehmann et al (1992) Nature 358:155-157).

For any given antigen, cryptic epitopes may also exist. Cryptic epitopes are those which can stimulate a T cell response when administered as a peptide but which fail to produce such a response when administered as a whole antigen. It may be that during processing of the antigen into peptides in the APC the cryptic epitope is destroyed.

The peptide of the invention may be an immunodominant epitope, a sub-dominant epitope or a cryptic epitope of 5T4.

Epitopes for an antigen may be identified by measuring the T cell response to overlapping peptides spanning a portion of the antigen (see below) when presented by APC. Such studies usually result in "nested sets" of peptides, and the minimal epitope for a particular T cell line/clone can be assessed by measuring the response to truncated peptides.

The minimal epitope for an antigen may not be the best epitope for practical purposes. It may well be that amino acids flanking the minimal epitope will be required for optimal binding to the MHC.

Identification of Epitopes

There are a number of methods known in the art to identify the T cell epitopes within a given antigen.

Naturally processed epitopes may be identified by mass spectrophotometric analysis of peptides eluted from antigen-loaded APC. These are APC that have either been encouraged to take up antigen, or have been forced to produce the protein intracellularly by transformation with the appropriate gene. Typically APC are incubated with protein either in solution or suitably targeted to the APC cell surface. After incubation at 37° C. the cells are lysed in detergent and the class II protein purified by, for example, affinity chromatography. Treatment of the purified MHC with a suitable chemical medium (for example, acid conditions) results in the elution of peptides from the MHC. This pool of peptides is separated and the profile compared with peptide from control APC treated in the same way. The peaks unique to the protein expressing/fed cells are analysed (for example by mass spectrometry) and the peptide fragments identified. This procedure usually generates information about the range of peptides (usually found in "nested sets") generated from a particular antigen by antigen processing.

Another method for identifying epitopes is to screen a synthetic library of peptides which overlap and span the length of the antigen in an iii vitro assay. For example, peptides which are 15 amino acids in length and which overlap by 5 or 10 amino acids may be used. The peptides are tested in an antigen presentation system which comprises antigen presenting cells and T cells. For example, the antigen presentation system may be a murine splenocyte preparation, a preparation of human cells from tonsil or PBMC. Alternatively, the antigen presentation system may comprise a particular T cell line/clone and/or a particular antigen presenting cell type.

T cell activation may be measured via T cell proliferation (for example using 3H-thymidine incorporation) or cytokine production. Activation of TH1-type CD4+ T cells can, for example be detected via IFNγ production which may be detected by standard techniques, such as an ELISPOT™ (ELISA) assay.

Overlapping peptide studies usually indicate the area of the antigen in which an epitope is located. The minimal epitope for a particular T cell can then be assessed by measuring the response to truncated peptides. For example if a response is obtained to the peptide comprising residues 1-15 in the overlapping library, sets which are truncated at both ends (i.e. 1-14, 1-13, 1-12 etc. and 2-15, 3-15, 4-15 etc.) can be used to identify the minimal epitope.

Polyepitope String

It has been found that a particularly effective way to induce an immune response to an antigen is by the use of a polyepitope string, which contains a plurality of antigenic epitopes from one or more antigens linked together. For example, for malaria, a polyepitope string of mainly malaria (*P. falciparum*) CD8 T cell peptide epitopes has been described which also expresses CD4 T cell epitopes from tetanus toxoid and from the 38 Kd mycobacterial antigen of various strains of *M. tuberculosis* and *M. bovis*.

The present invention also provides a polyepitope string comprising at least one peptide according to the present invention. The string may also comprise another epitope derivable from the 5T4 antigen or an epitope from another antigen—such as another TAA—or combinations thereof.

TAAs have been characterised either as membrane proteins or altered carbohydrate molecules of glycoproteins and glycolipids, however their functions remain largely unknown. One TAA family, the transmembrane 4 superfamily (TM4SF), usually has four well-conserved membrane-spanning regions, certain cysteine residues and short sequence motifs. There is evidence that TM4SF antigens exist in close association with other important membrane receptors including CD4 and CD8 of T cells (Imai & Yoshie (1993) J Immunol. 151, 6470-6481). It has also been suggested that TM4SF antigens may play a role in signal transduction which in turn, affects cell development, activation and motility. Examples of TM4SF antigens include human melanoma-associated antigen ME491, human and mouse leukocyte surface antigen CD37, and human lymphoblastic leukemia-associated TALLA-1 (Hotta, H. et al. (1988) Cancer Res. 48, 2955-2962; Classon, B. J. et al. (1989) J. Exp. Med. 169: 1497-1502; Tomlinson, M. G. et al. (1996) Mol. Immun. 33: 867-872; Takagi, S. et al. (1995) Int. J. Cancer 61: 706-715).

Further examples of TAAs also include, but are not limited to, TAAs in the following classes: cancer testis antigens (HOM-MEL-40), differentiation antigens (HOM-MEL-55), overexpressed gene products (HOM-MD-21), mutated gene products (NY-COL-2), splice variants (HOM-MD-397), gene amplification products (HOM-NSCLC-11) and cancer related autoantigens (HOM-MEL-2.4) as reviewed in Cancer Vaccines and Immunotherapy (2000) Eds Stem, Beverley and Carroll,, Cambridge University Press, Cambridge. Further examples include, MART-1 (Melanoma Antigen Recognised by T cells-1) MAGE-A (MAGE-A1, MAGE-A2, MAGE-A3, MAGE-A4, MAGE-A6, MAGE-A8, MAGE-A10, MAGE-A12), MAGE B (MAGE-B1- MAGE-B24), MAGE-C (MAGE-C1/CT7, CT10), GAGE (GAGE-1, GAGE-8, PAGE-1, PAGE-4, XAGE-1, XAGE-3), LAGE (LAGE-1a (1S), -1b(1L), NY-ESO-1), SSX (SSX1-SSX-5), BAGE, SCP-1, PRAME (MAPE), SART-1, SART-3, CTp11, TSP50, CT9/BRDT, gp100, MART-1, TRP-1, TRP-2, MELAN-A/MART-1, Carcinoembryonic antigen (CEA), prostate-specific antigen (PSA), MUCIN (MUC-1) and Tyrosinase. TAAs are reviewed in Cancer Immunology (2001) Kluwer Academic Publishers, The Netherlands.

Cell Penetrators

The present invention also provides a peptide epitope, or a polyepitope string in association with a cell penetrator.

Antigen presenting cells (such as dendritic cells) pulsed with peptides have proven effective in enhancing antitumour immunity (Celluzzi et al (1996) J. Exp. Med. 183 283-287; Young et al (1996) J. Exp. Med. 183 7-11). It has been shown that it is possible to prolong the presentation of a peptide by dendritic cells (and thus enhance antitumour immunity) by limiting it to a cell penetrating peptide (CPP) (Wang and Wang (2002) Nature Biotechnology 20 149-154).

A cell penetrator may be any entity which enhances the intracellular delivery of the peptide/polyepitope string to the antigen presenting cell. For example, the cell penetrator may be a lipid which, when associated with the peptide, enhances its capacity to cross the plasma membrane. Alternatively, the cell penetrator may be a peptide. Several cell penetrating peptide (CPPs) have been identified from proteins, including the Tat protein of HIV (Frankel and Pabo (1988) Cell 55 1189-1193), the VP22 protein of HSV (Elliott and O'Hare (1997) Cell 88 223-233) and fibroblast growth factor (Lin et al (1995) J. Biol. Chem. 270 14255-14258).

The term "associated with" is intended to include direct linkage, for example by a covalent bond. Examples of covalent bonds for lining amino acids include disulphide bridges and peptide bonds. In a preferred embodiment, the peptide/polyepitope string and a CPP are linked by a peptide bond to create a fusion protein.

The term also includes non-covalent linkage, such as association by electrostatic bonding, hydrogen bonding and van der Waals forces. The cell penetrator and peptide/polyepitope string may be associated without covalent or non-covalent bonding. For example the cell penetrator may be a lipid which encapsulates the peptide/polyepitope string (e.g. a liposome).

5T4

5T4 has been previously characterised, for example, in WO89/07947. The sequence of human 5T4 which appears in GenBank at accession no. Z29083. The peptide may also be derived from a 5T4 antigen from a different species, such as murine 5T4 (WO00/29428), canine 5T4 (WO01/36486) or feline 5T4 (SEQ ID No 1 presented herein). The peptide may also be derived from a naturally occurring variant of 5T4 found with a particular species, preferably a mammal. Such a variant may be encoded by a related gene of the same gene family, by an allelic variant of a particular gene, or represent an alternative splicing variant of the 5T4 gene.

A peptide derived from 5T4 from a different species or a splice variant may have a different amino acid sequence from the analogous human wild-type 5T4 peptide. However, as long as the peptide retains the same qualitative binding specificity as the human peptide (i.e. it binds in the peptide binding groove of an MHC molecule of the same haplotype) then it is still an epitope in accordance with the present invention.

Nucleic Acid

The present invention also relates to a nucleic acid sequence capable of encoding a peptide epitope or polyepitope string according to the first aspect of the invention.

A "nucleic acid", as referred to herein, may be DNA or RNA, naturally-occurring or synthetic, or any combination thereof. Nucleic acids according to the invention are limited only in that they serve the function of encoding a 5T4 peptide in such a way that it may be translated by the machinery of the cells of a host organism. Thus, natural nucleic acids may be modified, for example to increase the stability thereof. DNA and/or RNA, but especially RNA, may be modified in order to improve nuclease resistance of the members. For example, known modifications for ribonucleotides include 2'-O-methyl, 2'-fluoro, 2'-NH$_2$, and 2'-O-allyl. The modified nucleic acids according to the invention may comprise chemical modifications which have been made in order to increase the in vivo stability of the nucleic acid, enhance or mediate the delivery thereof, or reduce the clearance rate from the body. Examples of such modifications include chemical substitutions at the ribose and/or phosphate and/or base positions of a given RNA sequence. See, for example, WO 92/03568; U.S. Pat. No. 5,118,672; Hobbs et al., (1973) Biochemistry 12:5138; Guschlbauer et al., (1977) Nucleic Acids Res. 4:1933; Schibaharui et al., (1987) Nucleic Acids Res. 15:4403; Pieken et al., (1991) Science 253:314, each of which is specifically incorporated herein by reference.

The present invention also encompasses nucleic acids which will hybridise to a nucleic acid sequence capable of encoding a peptide epitope or polyepitope string according to the first aspect of the invention.

Stringency of hybridisation refers to conditions under which polynucleic acid hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na+ at 65-68 ° C. High stringency conditions can be provided, for example, by hybridisation in an aqueous solution containing 6×SSC, 5× Denhardt's, 1% SDS (sodium dodecyl sulphate), 0.1 Na+ pyrophosphate and 0.1 mg/ml denatured salmon sperm DNA as non specific competitor. Following hybridisation, high stringency washing may be done in several steps, with a final wash (about 30 min) at the hybridisation temperature in 0.2-0.1×SSC, 0.1% SDS.

Moderate stringency refers to conditions equivalent to hybridisation in the above described solution but at about 60-62° C. In that case the final wash is performed at the hybridisation temperature in 1×SSC, 0.1% SDS.

Low stringency refers to conditions equivalent to hybridisation in the above described solution at about 50-52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Given the guidance provided herein, the nucleic acids of the invention are obtainable according to methods well known in the art. For example, a DNA of the invention is obtainable by chemical synthesis, using polymerase chain reaction (PCR) or direct cleavage from a longer polynucleotide, such as the entire 5T4 coding sequence or a fragment thereof.

Chemical methods for synthesis of a nucleic acid of interest are known in the art and include triester, phosphite, phosphoramidite and H-phosphonate methods, PCR and other autoprimer methods as well as oligonucleotide synthesis on solid supports. These methods may be used if the entire nucleic acid sequence of the nucleic acid is known, or the sequence of the nucleic acid complementary to the coding strand is available. Alternatively, if the target amino acid sequence is known, one may infer potential nucleic acid sequences using known and preferred coding residues for each amino acid residue.

It is envisaged that the nucleic acid of the invention can be modified by nucleotide substitution, nucleotide deletion, nucleotide insertion or inversion of a nucleotide stretch, and any combination thereof. Such mutants can be used e.g. to produce a 5T4 peptide that has an amino acid sequence differing from the wild-type 5T4 epitope. Such a peptide is still a peptide in accordance with the present invention if it retains the capacity to act as a T cell epitope. Mutagenesis may be predetermined (site-specific) or random. A mutation which is not a silent mutation should not place sequences out of reading frames and preferably will not create complementary regions that could hybridise to produce secondary mRNA structure such as loops or hairpins.

Variants/fragments/homologues/derivatives

The present invention encompasses the use of nucleotide and amino acid sequences and variants, homologues, derivatives and fragments thereof.

The term "variant" is used to mean a naturally occurring polypeptide or nucleotide sequence which differs from a wild-type sequence.

The term "fragment" indicates that a polypeptide or nucleotide sequence comprises a fraction of a subject sequence. Preferably the sequence comprises at least 50%, more preferably at least 65%, more preferably at least 80%, more preferably at least 90%, most preferably at least 90% of the subject sequence. If the fragment is a fragment of an amino acid then preferably the fragments are 6-12 amino acids in length. More preferably, the fragments are 8, 9 or 10 amino acids in length. By way of example, SEQ ID NO: 6 and SEQ ID NO: 8 are fragments of SEQ ID NO: 4;1 SEQ ID NO: 7 is a fragment of SEQ ID NO: 5.

The term "homologue" means an entity having a certain homology with the subject amino acid sequences and the subject nucleotide sequences. Here, the term "homology" can be equated with "identity".

In the present context, a homologous sequence is taken to include an amino acid sequence, which may be at least 75, 85 or 90% identical, preferably at least 95 or 98% identical to the subject sequence. Typically, the homologues will comprise the same activity as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence, which may be at least 75, 85 or 90% identical, preferably at least 95 or 98% identical to the subject sequence. Typically, the homologues will comprise the same activity as the subject sequence. Although homology can also be considered in terms of similarity (i.e. amino acid residues having similar chemical properties/functions), in the context of the present invention it is preferred to express homology in terms of sequence identity.

Homology comparisons may be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix—such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues, which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of. the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example, according to the Table below. Amino acids in the same block in the second column and preferably in the same line in the third column may be substituted for each other:

| ALIPHATIC | Non-polar | G A P |
| --- | --- | --- |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution—such as basic for basic, acidic for acidic, polar for polar etc. Non-homologous substitution may also occur i.e. from one class of residue to another or alternatively involving the inclusion of unnatural amino acids—such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids—such as trifluorotyrosine*, p-Cl-phenylalanine*, p-Br-phenylalanine*, p-I-phenylalafiine*, L-allyl-glycine*, β-alanine*, L-α-amino butyric acid*, L-γ-amino butyric acid*, L-α-amino isobutyric acid*, L-ϵ-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe)—such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups—such as methyl, ethyl or propyl groups—in addition to amino acid spacers—such as glycine or β-alanine residues. A further form of variation involves the presence of one or more amino acid residues in peptoid form will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example, Simon R J et al., PNAS (1992) 89(20), 9367-9371 and Horwell D C, Trends Biotechnol. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences may be modified by any method available in the art. Such modifications may be carried out to enhance the in vivo activity or life span of nucleotide sequences useful in the present invention.

Vector System

The nucleic acid sequence of the present invention may be delivered to a cell by way of a vector system.

As used herein, a "vector" may be any agent capable of delivering or maintaining nucleic acid in a host cell, and includes viral vectors, plasmids, naked nucleic acids, nucleic acids complexed with polypeptide or other molecules and nucleic acids immobilised onto solid phase particles. Such vectors are described in detail below. It will be understood that the present invention, in its broadest form, is not limited to any specific vector for delivery of the 5T4 peptide-encoding nucleic acid.

The vector may be a prokaryotic or eukaryotic vector.

Nucleic acids encoding 5T4 epitopes and polyepitope strings in accordance with the present invention can be delivered by viral or non-viral techniques.

Non-viral delivery systems include but are not limited to DNA transfection methods. Here, transfection includes a process using a non-viral vector to deliver a 5T4 gene to a target mammalian cell.

Typical transfection methods include electroporation, nucleic acid biolistics, lipid-mediated transfection, compacted nucleic acid-mediated transfection, liposomes, immunoliposomes, lipofectin, cationic agent-mediated, cationic facial amphiphiles (CFAs) (Nature Biotechnology 1996 14; 556), multivalent cations such as spermine, cationic lipids or polylysine, 1, 2,-bis (oleoyloxy)-3-(trimethylammonio) propane (DOTAP)-cholesterol complexes (Wolff and Trubetskoy 1998 Nature Biotechnology 16: 421) and combinations thereof.

Non-viral delivery systems may also include, but are not limited to, bacterial delivery systems. The use of bacteria as anticancer agents and as delivery agents for anticancer drugs has been reviewed in Expert Opin Biol Ther 2001 March;1 (2):291-300.

Suitable bacteria include, but are not limited to, bacterial pathogens and non-pathogenic commensal bacteria. By way of example, suitable genera may be selected from *Salmonella, Mycobacterium, Yersinia, Shigella, Listeria* and *Brucella*. Recent advances in the pathogenesis and molecular biology of these bacteria have allowed the rational development of new and improved bacterial carriers and more effective gene expression systems. These advances have improved the performance and versatility of these delivery systems.

The bacteria may be invasive intracellular bacteria that are able to transfer eukaryotic expression plasmids into mammalian host cells in vitro and in vivo. Plasmid transfer may take place when the recombinant bacterium dies within the host cell, either due to metabolic attenuation or induction of autolysis. Alternatively, antibiotics may be used and spontaneous transfer has also been observed, indicating that this phenomenon might also occur under physiological conditions. Plasmid transfer has been reported for *Shigella flexneri, Salmonella typhinurium, S. typhi, Listeria monocytogenes* and recombinant *Escherichia coli*, but other invasive bacteria may also be used.

Bacteria may be used for DNA vaccine delivery. Such bacteria may enter the host cell cytosol after phagocytosis, for example, *Shigella* and *Listeria*, or they remain in the phagosomal compartment—such as *Salmonella*. Both intracellular localisations may be suitable for successful delivery of DNA vaccine vectors.

The bacterial delivery systems may utilise *Mycobacterium* in the form of non pathogenic Mycobacterium strains, genetic transfer systems in the form of cloning and expression vectors, and related technologies to provide products containing, for example, non toxic immuno-regulating *Mycobacterium* adjuvants, non toxic immuno-stimulating exogenous antigens specific for a variety of diseases, and non toxic amounts of cytokines that boost the TH-1 pathway (Tunis Med 2001 February;79(2):65-81).

*Salmonella* strains—such as attenuated strains—which comprise defined gene deletions, may be used as suitable delivery systems—such as the delivery of antigens. A number of strategies for delivery by these strains have been attempted, ranging from plasmid-based to chromosomal integration systems. By way of example, Rosenkranz et al. Vaccine 2003, 21(7-8), 798-801 describe eukaryotic expression plasmids encoding cytokines, and assessed their capacity to modulate immune responses in different experimental models. Plasmids encoding mouse IL-4 and IL-18 under cytomegalovirus promoter were constructed and transformed into live attenuated *Salmonella enterica* serovar Typhi strain CVD 908-htrA, and *Salmonella enterica* serovar Typhimurium strain SL3261.

The use of attenuated *Salmonella typhimurium* as a potential gene delivery vector has been reviewed in Anticancer Res 2002, 22(6A):3261-6.

*Brucella abortus* may also be used as a suitable delivery system as described by Vemulapalli et al. Infect Immun (2000) 68(6):3290-6. Brucella abortus strain RB51 is a stable, rough, attenuated mutant widely used as a live vaccine for bovine brucellosis. This strain may be used as a delivery vector, for example, in the delivery of protective antigens of other intracellular pathogens to which the induction of a strong Th1 type of immune response is needed for effective protection.

Boyd et al. Eur J Cell Biol (2000) 79 (10) 659-71 describe the use of *Yersinia enterocolitica* for the delivery of proteins into a wide range of cell types. *Y. enterocolitica* translocates virulence proteins, called Yop effectors, into the cytosol of eukaryotic cells. No limit to the range of eukaryotic cells into which *Y. enterocolitica* can translocate Yops was reported. The Yop effectors YopE, YopH and YopT were each cytotoxic for the adherent cell types tested, showing that not only is *Y. enterocolitica* not selective in its translocation of particular Yop effectors into each cell type, but also that the action of these Yop effectors is not cell type specific. To use the *Yersinia* translocation system for broad applications, a *Y. enterocolitica* translocation strain and vector for the delivery of heterologous proteins into eukaryotic cells was constructed. This strain and vector combination lacks the translocated Yop effectors and allows delivery into eukaryotic cells of heterologous proteins fused to the minimal N-terminal secretion/translocation signal of YopE.

U.S. Pat. No. 5,965,381 describes a recombinant *Yersinia* for the delivery of proteins into eukaryotic cells. Such *Yersinia* are deficient in the production of functional effector proteins, but are endowed with a functional secretion and translocation system.

Cell adhesion molecules are a large group of molecules involved in a variety of cell-to-cell and cell-to-extra-cellular matrix (ECM) interactions and are exploited by a number of pathogenic micro-organisms as receptors for cell entry. These molecules may be used for the targeting and uptake of both gene and drug delivery systems. Cell adhesion molecules and their use in gene transfer has been reviewed in Adv Drug Deliv Rev 2000 Nov. 15;44(2-3): 135-52.

The gene gun delivery system may also be used for the delivery of DNA, which is a highly reliable method compared to intramuscular inoculation (Jpn J Pharmacol 2000 July;83 (3):167-74).

Viral delivery systems include but are not limited to adenovirus vectors, adeno-associated viral (AAV) vectors, herpes viral vectors, retroviral vectors, lentiviral vectors or baculoviral vectors, venezuelan equine encephalitis virus (VEE), poxviruses such as: canarypox virus (Taylor et al 1995 Vaccine 13:539-549), entomopox virus (Li Y et al 1998 XII$^{th}$ International Poxvirus Symposium p144. Abstract), penguine pox (Standard et al. J Gen Virol. 1998 79:1637-46) alphavirus, and alphavirus based DNA vectors.

Examples of retroviruses include but are not limited to: murine leukaemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukaemia virus (Mo-MLV), FBR murine osteosarcoma virus (FBR MSV), Moloney murine sarcoma virus (Mo-MSV), Abelson murine leukaemia virus (A-MLV), Avian myelocytomatosis virus-29 (MC29), and Avian erythroblastosis virus (AEV).

A detailed list of retroviruses may be found in Coffin et al ("Retroviruses" 1997 Cold Spring Harbour Laboratory Press Eds: J M Coffin, S M Hughes, H E Varmus pp 758-763).

Lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine ahthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells (Lewis et al 1992 EMBO. J 11: 3053-3058; Lewis and Emerman 1994 J. Virol. 68: 510-516). In contrast, other retroviruses—such as MLV—are unable to infect non-dividing cells such as those that make up, for example, muscle, brain, lung and liver tissue.

The vector of the present invention may be configured as a split-intron vector. A split intron vector is described in PCT patent applications WO 99/15683 and WO 99/15684.

If the features of adenoviruses are combined with the genetic stability of retroviruses/lentiviruses then essentially the adenovirus can be used to transduce target cells to become transient retroviral producer cells that could stably infect neighbouring cells. Such retroviral producer cells engineered to express 5T4 antigen can be implanted in organisms such as animals or humans for use in the treatment of angiogenesis and/or cancer.

The vector of the present invention may be configured as a psuedotyped vector.

In the design of retroviral vectors it may be desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus.

The term pseudotyping means incorporating in at least a part of, or substituting a part of, or replacing all of, an env gene of a viral genome with a heterologous env gene, for example an env gene from another virus. Pseudotyping is not a new phenomenon and examples may be found in WO 99/61639, WO-A-98/05759, WO-A-98/05754, WO-A-97/17457, WO-A-96/09400, WO-A-91/00047 and Mebatsion et al 1997 Cell 90, 841-847.

Pseudotyping can improve retroviral vector stability and transduction efficiency. A pseudotype of murine leukemia virus packaged with lymphocytic choriomeningitis virus (LCMV) has been described (Miletic et al (1999) J. Virol. 73:6114-6116) and shown to be stable during ultracentrifugation and capable of infecting several cell lines from different species.

Poxvirus Vectors

TAAs are weakly immunogenic, being recognised as "self" by the immune system and thus tolerated to a large extent. The use of poxvirus vectors is sometimes able to cause the antigens to be presented such that this tolerance may be overcome at least in part, (especially if immune evasion genes are deleted—see below) thus enabling a host to raise an immune response.

Poxvirus vectors are preferred for use in the present invention. Pox viruses are engineered for recombinant gene expression and for the use as recombinant live vaccines. This entails the use of recombinant techniques to introduce nucleic acids encoding foreign antigens into the genome of the pox virus. If the nucleic acid is integrated at a site in the viral DNA which is non-essential for the life cycle of the virus, it is possible for the newly produced recombinant pox virus to be infectious, that is to say to infect foreign cells and thus to express the integrated DNA sequence. The recombinant pox virus prepared in this way can be used as live vaccines for the prophylaxis and/or treatment of pathologic and infectious disease.

Expression of 5T4 peptide(s) in recombinant pox viruses, such as vaccinia viruses, requires the ligation of vaccinia promoters to the nucleic acid encoding the 5T4 peptide(s). Plasmid vectors (also called insertion vectors), have been constructed to insert nucleic acids into vaccinia virus through homologous recombination between the viral sequences flanking the nucleic acid in a donor plasmid and homologous sequence present in the parental virus (Mackett et al 1982 PNAS 79: 7415-7419). One type of insertion vector is composed of: (a) a vaccinia virus promoter including the transcriptional initiation site; (b) several unique is restriction endonuclease cloning sites located downstream from the transcriptional start site for insertion of nucleic acid; (c) nonessential vaccinla virus sequences (such as the Thymidine Kinase (TK) gene) flanking the promoter and cloning sites which direct insertion of the nucleic acid into the homologous nonessential region of the virus genome; and (d) a bacterial origin of replication and antibiotic resistance marker for replication and selection in E. Coli. Examples of such vectors are described by Mackett (Mackett et al 1984, J. Virol. 49: 857-864).

The isolated plasmid containing the nucleic acid to be inserted is transfected into a cell culture, e.g., chick embryo fibroblasts, along with the parental virus, e.g., poxvirus. Recombination between homologous pox DNA in the plasmid and the viral genome respectively results in a recombinant poxvirus modified by the presence of the promoter-gene construct in its genome, at a site which does not affect virus viability.

As noted above, the nucleic acid is inserted into a region (insertion region) in the virus which does not affect virus viability of the resultant recombinant virus. Such regions can be readily identified in a virus by, for example, randomly testing segments of virus DNA for regions that allow recombinant formation without seriously affecting virus viability of the recombinant. One region that can readily be used and is present in many viruses is the thymidine kinase (TK) gene. For example, the TK gene has been found in all pox virus genomes examined [leporipoxvirus: Upton, et al J. Virology 60:920 (1986) (shope fibroma virus); capripoxvirus: Gershon, et al J. Gen. Virol. 70:525 (1989) (Kenya sheep-1); orthopoxvirus: Weir, et al J. Virol 46:530 (1983) (vaccinia); Esposito, et al Virology 135:561 (1984) (monkeypox and variola virus); Hruby, et al PNAS, 80:3411 (1983) (vaccinia); Kilpatrick, et al Virology 143:399 (1985) (Yaba monkey tumour virus); avipoxvirus: Binns, et al J. Gen. Virol 69:1275 (1988) (fowlpox); Boyle, et al Virology 156:355 (1987) (fowlpox); Schnitzlein, et al J. Virological Method, 20:341 (1988) (fowlpox, quailpox); entomopox (Lytvyn, et al J. Gen. Virol 73:3235-3240 (1992)].

In vaccinia, in addition to the TK region, other insertion regions include, for example, HindIII M.

In fowlpox, in addition to the TK region, other insertion regions include, for example, BamHI J [Jenkins, et al AIDS Research and Human Retroviruses 7:991-998 (1991)] the EcoRI-HindIII fragment, BamHI fragment, EcoRV-HindII fragment, BamHI fragment and the HindIII fragment set forth in EPO Application No. 0 308 220 A1. [Calvert, et al J. of Virol 67:3069-3076 (1993); Taylor, et al Vaccine 6:497-503 (1988); Spehner, et al (1990) and Boursnell, et al J. of Gen. Virol 71:621-628 (1990)].

In swinepox preferred insertion sites include the thymidine kinase gene region.

A promoter can readily be selected depending on the host and the target cell type. For example in poxviruses, pox viral promoters should be used, such as the vaccinia 7.5K, or 40K or fowlpox C1. Artificial constructs containing appropriate pox sequences can also be used. Enhancer elements can also be used in combination to increase the level of expression. Furthermore, the use of inducible promoters, which are also well known in the art, are preferred in some embodiments.

Foreign gene expression can be detected by enzymatic or immunological assays (for example, immuno-precipitation, radioimmunoassay, or immunoblotting). Naturally occurring membrane glycoproteins produced from recombinant vaccinia infected cells are glycosylated and may be transported to the cell surface. High expressing levels can be obtained by using strong promoters.

Other requirements for viral vectors for use in vaccines include good immunogenicity and safety. MVA is a replication-impaired vaccinia strain with a good safety record. In most cell types and normal human tissue, MVA does not replicate. Replication of MVA is observed in a few transformed cell types such as BHK21 cells. Carroll et al (1997) have shown that the recombinant MVA is equally as good as conventional recombinant vaccinia vectors at generating a protective CD8+T cell response and is an efficacious alternative to the more commonly used replication competent vaccinia virus. The vaccinia virus strains derived from MVA, or independently developed strains having the features of MVA which make MVA particularly suitable for use in a vaccine, are also suitable for use in the present invention.

Preferably, the vector is a vaccinia virus vector such as MVA or NYVAC. Most preferred is the vaccinia strain modified virus ankara (MVA) or a strain derived therefrom. Alternatives to vaccinia vectors include avipox vectors such as fowlpox or canarypox known as ALVAC and strains derived therefrom which can infect and express recombinant proteins in human cells but are unable to replicate.

In one aspect of the present invention at least one immune evasion gene is deleted from the poxvirus vector.

Viruses, especially large viruses such a poxviruses which have an extensive coding capacity and can thus encode a variety of genes, have developed a number of techniques for evading the immune system of their hosts. For example, they are able to evade non-specific defences such as complement, interferons and the inflammatory response, as well as to interfere with or block the function of cytokines. A number of these immune evasion polypeptides have been deleted from MVA, with the exception of the interferon resistance protein in the left terminal region.

Poxviruses in general, being large DNA viruses which establish acute, rather than latent, infections. They encode so many antigenic proteins that antigenic variation is difficult, thus relying on active immune evasion to protect themselves from the mammalian immune system. They possess a number of genes which encode polypeptides which are responsible for interfering with a number of aspects of the immune system: they disrupt interferon action, interfere with complement, cytokine activity, inflammatory responses and CTL recognition (for a review, Smith et al., (1997) Immunol Rev 159:137-154). Removal of these proteins is beneficial in promoting the ability of weak immunogens encoded on a poxvirus vector to elicit an immune response in a subject.

An immune evasion gene or polypeptide is a gene, or its product, which assists the virus in s evading the mammalian immune system. Preferably, the gene or gene product interferes with the working of the immune system, at least one level. This may be achieved in a number of ways, such as by interfering in signalling pathways by providing competitors for signalling molecules, by providing soluble cytokine receptor mimics and the like.

Immune evasion genes include, but are not limited to, the following:

Interferon evasion genes. Vaccinia possesses at least three genes which interfere with IFN action. The E3L gene expresses a 25 Kd polypeptide which competes with PI protein kinase for binding to dsRNA, an event which leads to activation of P1, phosphorylation of eIF2$\alpha$ and resultant failure of translation initiation complex assembly. This pathway is ordinarily responsive to IFN activation, but is impeded by E3L expression thus allowing translation initiation to proceed unimpeded.

The K3L gene expresses a 10.5 Kd polypeptide which also interferes with P1 activity, since it is effectively an eIF2 mimic and acts as a competitor for P1 protein kinase. Its mode of action is thus similar to E3L.

The A18R gene is predicted to encode a helicase, which appears to interfere with the 2',5'-oligoadenylate pathway, which is in turn IFN responsive. 2',5'-A activates RNAse L, which acts to prevent viral translation. Expression of A18R appears to reduce 2',5'-A levels in infected cells.

Complement. The product of the B5R gene of vaccinia is known to be highly related to factor H, a regulator of the alternative complement pathway. This pathway may be activated by antigen alone, unlike the classical pathway. The B5R gene product thus may interfere with the alternative complement pathway.

The C21L gene is in turn related to C4b-binding protein in humans, and interacts with cells bearing C4b on the surface to prevent binding to the CR1 complement receptor.

Solible Cytokine Receptoirs. The product of the vaccinia WR B15R gene (B16R in Copenhagen strain vaccinia) is related to IL1-R.

The WR gene ORF SalF19R, A53R in Copenhagen strain vaccinia, encodes a TNF receptor. However, in wild-type virus both of these genes are believed to be inactive due to fragmentation of the ORFs.

The B8R gene is believed to encode a soluble IFN-$\gamma$ receptor, providing the virus with yet another IFN evasion mechanism.

Inflammation. A number of genes are believed to be involved in the prevention of inflammatory responses to viral infection. These include A44L, K2L, B13R and B22R.

In one aspect of the present invention, the majority of the immune evasion genes are deleted from the recombinant poxvirus vector. Preferably, all the immune evasion genes are deleted. Thus, in one aspect of the present invention, the recombinant poxvirus vector is a recombinant MVA vector in which the K3L interferon resistance protein gene has been disrupted or deleted.

Preferred are poxviruses which are non-hazardous to the intended subject. Thus, for example, for use in humans, poxviruses which are either host-range restricted, such as avipox viruses, or otherwise attenuated, such as attenuated strains of vaccinia (including NYVAC and MVA) are preferred. Most preferred are attenuated vaccinia virus strains, although non-vaccinia strains are usefully employed in subjects with pre-existing smallpox immunity.

A construct which contains at least one nucleic acid which codes for 5T4 epitope(s) flanked by MVA DNA sequences adjacent to a naturally occurring deletion, e.g. deletion II, within the MVA genome, is introduced into cells infected with MVA, to allow homologous recombination.

Once the construct has been introduced into the eukaryotic cell and the 5T4 epitope DNA has recombined with the viral DNA, the desired recombinant vaccinia virus, can be isolated, preferably with the aid of a marker (Nakano et al Proc. Natl. Acad. Sci. USA 79, 1593-1596 [1982], Franke et al Mol. Cell. Biol. 1918-1924 [1985], Chakrabarti et al Mol. Cell. Biol. 3403-3409 [1985], Fathi et al Virology 97-105 [1986]).

The construct to be inserted can be linear or circular. A circular DNA is preferred, especially a plasmid. The construct contains sequences flanking the left and the right side of a naturally occurring deletion, e.g. deletion II, within the MVA genome (Altenburger, W., Suter, C. P. and Altenburger J. (1989) Arch. Virol. 105, 15-27). The foreign DNA sequence is inserted between the sequences flanking the naturally occurring deletion.

For the expression of at least one nucleic acid, it is necessary for regulatory sequences, which are required for the transcription of the nucleic acid to be present upstream of the nucleic acid. Such regulatory sequences are known to those skilled in the art, and includes for example those of the vaccinia 11 kDa gene as are described in EP-A-198,328, and those of the 7.5 kDa gene (EP-A-110,385).

The construct can be introduced into the MVA infected cells by transfection, for example by means of calcium phosphate precipitation (Graham et al Virol. 52, 456-467 [1973; Wigler et al Cell 777-785 [1979] by means of electroporation (Neumann et al EMBO J. 1, 841-845 [1982]), by microinjection (Graessmann et al Meth. Enzymology 101, 482-492 (1983)), by means of liposomes (Straubinger et al Methods in Enzymology 101, 512-527 (1983)), by means of spheroplasts (Schaffner, Proc. Natl. Acad. Sci. USA 77, 2163-2167 (1980)) or by other methods known to those skilled in the art. Transfection by means of liposomes is preferred.

The recombinant priming and boosting vectors of the present invention can have a tropism for a specific cell type in the mammal. By way of example, the recombinant vectors of the present invention can be engineered to infect professional APCs such as dendritic cells and macrophages. Dendritic cells are known to be orchestrators of a successful immune response especially that of a cell mediated response. It has been shown that ex vivo treatment of dendritic cells with antigen or viral vectors containing such a target antigen, will induce efficacious immune responses when infused into syngeneic animals or humans (see Nestle FO, et al. Vaccination of melanoma patients with peptide- or tumor lysate-pulsed dendritic cells, Nat Med. 1998 March;4(3):328-32 and Kim C J, et al. Dendritic cells infected with poxviruses encoding MART-1/Melan A sensitize T lymphocytes in vitro.

J Immunother. 1997 July;20(4):276-86. The recombinant vectors can also infect tumour cells. Alternatively, the recombinant vectors are able to infect any cell in the mammal.

Other examples of vectors include ex vivo delivery systems, which include but are not limited to DNA transfection methods such as electroporation, DNA biolistics, lipid-mediated transfection and compacted DNA-mediated transfection.

The vector may be a plasmid DNA vector. As used herein, "plasmid" refers to discrete elements that are used to introduce heterologous DNA into cells for either expression or replication thereof. Selection and use of such vehicles are well within the skill of the artisan.

Pulsed Cells

The present invention also provides cells pulsed with peptides of the first aspect of the invention.

Preferably the cells to be pulsed are capable of expressing MHC class I or class II.

MHC class I molecules can be expressed on nearly all cell types, but expression of MHC class II molecules is limited to so-called "professional" antigen presenting cells (APCs); B cells, dendritic cells and macrophages. However, expression of MHC class II can be induced on other cell types by treating with IFNγ.

Expression of MHC class I or MHC class II molecules can also be achieved by genetic engineering (i.e. provision of a gene encoding the relevant MHC molecule to the cell to be pulsed). This approach has the advantage that an appropriate MHC haplotype(s) can be chosen which bind specifically to the peptide(s).

Preferably the cell to be pulsed is an antigen presenting cell, i.e. a cell which, in a normal immune response, is capable of processing an antigen and presenting it at the cell surface in conjunction with an MHC molecule. Antigen presenting cells include B cells, macrophages and dendritic cells. In an especially preferred embodiment, the cell is a dendritic cell.

Preferably the cell is capable of expressing an MHC molecule which binds a peptide according to the first aspect of the invention in its peptide binding groove. For example, the cell may express one of the following HLA restriction elements: B8, Cw7 or A2 (for MHC class I).

Peptide pulsing protocols are known in the art (see for example Redchenko and Rickinson (1999) J. Virol. 334-342; Nestle et al (1998) Nat. Med. 4 328-332; Tjandrawan et al (1998) J. Immunotherapy 21 149-157). For example, in a standard protocol for loading dendritic cells with peptides, cells are incubated with peptide at 50 μg/ml with 3 μg/ml β-2 microglobulin for two hours in serum free medium. The unbound peptide is then washed off.

The pulsed cell of the present invention may be used as a vaccine, for example to stimulate a prophylactic or therapeutic anti-5T4 immune response.

The present invention therefore also provides a method for treating and/or preventing a disease which comprises the step of administering a peptide-pulsed cell to a subject in need of same.

Vaccine/Pharmaceutical Composition

The present invention also provides a vaccine/pharmaceutical composition comprising a peptide epitope, a polyepitope string,, a nucleic acid sequence, a vector system and/or a cell according to previous aspects of the invention.

The vaccine/pharmaceutical composition may be for prophylactic or therapeutic use.

The vaccine may by prepared as an injectable, either as liquid solution or suspension; solid form suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP),N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminium hydroxide, aluminium phosphate, aluminium potassium sulphate (alum), beryllium sulphate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminium hydroxide), or a mixture of Amphigen and Alhydrogel are used. Only aluminium hydroxide is approved for human use.

The proportion of immunogen and adjuvant can be varied over a broad range so long as both are present in effective amounts. For example, aluminium hydroxide can be present in an amount of about 0.5% of the vaccine mixture ($Al_2O_3$ basis). Conveniently, the vaccines are formulated to contain a final concentration of immunogen in the range of from 0.2 to 200 μg/ml, preferably 5 to 50 μg/ml, most preferably 15 μg/ml.

After formulation, the vaccine may be incorporated into a sterile container which is then sealed and stored at a low temperature, for example 4° C., or it may be freeze-dried. Lyophilisation permits long-term storage in a stabilised form.

The vaccine may be administered in a convenient manner such as by the oral, intravenous (where water soluble), intramuscular, subcutaneous, intranasal, intradermal or suppository routes or implanting (e.g. using slow release molecules).

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Capsules, tablets and pills for oral administration to a patient may be provided with an enteric coating comprising, for example, EUDRAGIT™ coating "S", EUDRAGIT™ coating "L", cellulose acetate, cellulose acetate phthalate or hydroxypropylmethyl cellulose.

5T4 peptides may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

Heterologous Vaccination Regimes

Regimes for administration of vaccines/pharmaceutic compositions according to the present invention may be determined by conventional efficacy testing. Especially preferred, however, are regimes which include successive priming and boosting steps. It is observed that such regimes achieve superior breaking of immune tolerance and induction of T cell responses (see Schneider et al., 1998 Nat Med 4:397-402).

Prime-boost regimes may be homologous (where the same composition is administered in subsequent doses) or heterologous (where the priming and boosting compositions are different). For example, the priming composition may be a non-viral vector (such as a plasmid) encoding a 5T4 antigen and the boosting composition may be a viral vector (such as a poxvirus vector) encoding a 5T4 antigen, wherein either or both of said "5T4 antigens" is an epitope or polyepitope string of the present invention.

Diagnostic Methods

The present invention also provides an agent capable of binding specifically to a peptide according to the present invention and/or a nucleic acid sequence which encodes such a peptide.

An agent is considered to "bind specifically" to a peptide/nucleic acid sequence of the present invention if there is a greater than 10 fold difference, and preferably a 25, 50 or 100 fold difference between the binding of the agent to a peptide/nucleic acid sequence of the present invention and another peptide/nucleic acid sequence.

The agent may be any compound capable of binding specifically to a peptide and/or a nucleic acid sequence. The term "compound" refers to a chemical compound (naturally occurring or synthesised), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule.

Preferably the agent is identifiable by screening a library of candidate compounds. Libraries of compounds may be screened in multi-well plates (e.g., 96-well plates), with a different test compound in each well. In particular, the library of candidate compounds may be a combinatorial libraries. A variety of combinatorial libraries of random-sequence oligonucleotides, polypeptides, or synthetic oligomers have been proposed and number of small-molecule libraries have also been developed. Combinatorial libraries of oligomers may be formed by a variety of solution-phase or solid-phase methods in which mixtures of different subunits are added stepwise to growing oligomers or parent compound, until a desired oligomer size is reached (typically hexapeptide or heptapeptide). A library of increasing complexity can be formed in this manner, for example, by pooling multiple choices of reagents with each additional subunit step. Alternatively, the library may be formed by solid-phase synthetic methods in which beads containing different-sequence oligomers that form the library are alternately mixed and separated, with one of a selected number of subunits being added to each group of separated beads at each step. Libraries, including combinatorial libraries are commercially available from pharmaceutical companies and speciality library suppliers.

Where the agent recognises a nucleic acid according to the present invention, the agent may comprise an antisense sequence.

Where the agent recognises a peptide according to the present invention, the agent may comprise an MHC molecule or part thereof which comprises the peptide binding groove. Alternatively the agent may comprise an anti-peptide antibody.

As used herein, "antibody" includes a whole immunoglobulin molecule or a part thereof or a bioisostere or a mimetic thereof or a derivative thereof or a combination thereof. Examples of a part thereof include: Fab, F(ab)'$_2$, and Fv. Examples of a bioisostere include single chain Fv (ScFv) fragments, chimeric antibodies, bifunctional antibodies.

The term "mimetic" relates to any chemical which may be a peptide, polypeptide, antibody or other organic chemical which has the same binding specificity as the antibody.

The term "derivative" as used herein in relation to antibodies includes chemical modification of an antibody. Illustrative of such modifications would be replacement of hydrogen by an alkyl, acyl, or amino group.

A whole immunoglobulin molecule is divided into two regions: binding (Fab) domains that interact with the antigen and effector (Fc) domains that signal the initiation of processes such as phagocytosis. Each antibody molecule consists of two classes of polypeptide chains, light (L) chains and heavy (H) chains. A single antibody has two identical copies of the L chain and two of the H chain. The N-terminal domain from each chain forms the variable regions, which constitute the antigen-binding sites. The C-terminal domain is called the constant region. The variable domains of the H ($V_H$) and L ($V_L$) chains constitute an Fv unit and can interact closely to form a single chain Fv (ScFv) unit. In most H chains, a hinge region is found. This hinge region is flexible and allows the Fab binding regions to move freely relative to the rest of the molecule. The hinge region is also the place on the molecule most susceptible to the action of protease which can split the antibody into the antigen binding site (Fab) and the effector (Fc) region.

The domain structure of the antibody molecule is favourable to protein engineering, facilitating the exchange between molecules of functional domains carrying antigen-binding activities (Fabs and Fvs) or effector finctions (Fc). The structure of the antibody also makes it easy to produce antibodies with an antigen recognition capacity joined to molecules such as toxins, lymphocytes or growth factors.

Chimeric antibody technology involves the transplantation of whole mouse antibody variable domains onto human antibody constant domains. Chimeric antibodies are less immunogenic than mouse antibodies but they retain their antibody specificity and show reduced HAMA responses.

In chimeric antibodies, the variable region remains completely murine. However, the structure of the antibody makes it possible to produce variable regions of comparable specificity which are predominantly human in origin. The antigen-combining site of an antibody is formed from the six complementarity-determining regions (CDRs) of the variable portion of the heavy and light chains. Each antibody domain consists of seven antiparallel β-sheets forming a β-barrel with loops connecting the β-strands. Among the loops are the CDR regions. It is feasible to more the CDRs and their associated specificity from one scaffolding β-barrel to another. This is called CDR-grafting. CDR-grafted antibodies appear in early clinical studies not to be as strongly immunogenic as either mouse or chimeric antibodies. Moreover, mutations may be made outside the CDR in order to increase the binding activity thereof, as in so-called humanised antibodies. Fab, Fv, and single chain Fv (ScFv) fragments with VH and VL joined by a polypeptide linker exhibit specificities and affinities for antigen similar to the original monoclonal antibodies. The ScFv fusion proteins can be produced with a non-antibody molecule attached to either the amino or carboxy terminus. In these molecules, the Fv can be used for specific targeting of the attached molecule to a cell expressing the appropriate antigen. Bifunctional antibodies can also be created by engineering two different binding specificities into a single antibody chain. Bifunctional Fab, Fv and ScFv antibodies may comprise engineered domains such as CDR grafted or humanised domains.

Procedures for identifying, characterising, cloning and engineering polyclonal and monoclonal antibodies and their derivatives are well established, for example using hybridomas derived from mice or transgenic mice, phage-display libraries or scFv libraries. Genes encoding immunoglobulins or immunoglobulin-like molecules can be expressed in a variety of heterologous expression systems. Large glycosylated proteins including immunoglobulins are efficiently secreted and assembled from eukaryotic cells, particularly mammalian cells. Small, non-glycosylated fragments such as Fab, Fv, or scFv fragments can be produced in functional form in mammalian cells or bacterial cells.

The agent may recognise the peptide/nucleic acid of the present invention alone, or in conjunction with another compound. For example, the agent may be capable or binding specifically to the peptide when presented by an MHC molecule. In this case, the agent of the present invention may comprise a T cell receptor molecule or part thereof.

The T cell receptor may be associated with another molecule such as CD4 (for MHC class II epitopes) or CD8 (for MHC class I epitopes). Alternatively, or in addition, the receptor may be associated with CD3.

If the agent occurs naturally in the human body, then preferably the agent of the present invention is in a substantially isolated form.

The present invention also provides a method which comprises the step of detecting the presence of a peptide, nucleic acid or agent of the present invention in a subject.

In a preferred embodiment, the method is used to detect the presence of T cells capable of specifically recognising a peptide epitope according to the present invention in conjunction with an MHC molecule.

The diagnostic method may, for example, be for diagnosing or monitoring the progression of a disease or for monitoring the progression of an immune response in a subject.

As mentioned above, as an immune response progresses, the dominance of particular epitopes may change, and subdominant epitopes can predominate. Thus by detecting the presence of a particular epitope, or a TCR/T cell capable of recognising such an epitope, information can be gained about the progression of the immune response.

The method may be carried out in vivo, or more preferably on an ex vivo sample.

Thus the present invention also provides a diagnostic method which comprises the following steps:
(i) isolating a sample from a subject;
(ii) detecting in the sample ex vivo the presence of T cells capable of specifically recognising a peptide epitope according to the present invention in conjunction with an MHC molecule.

In a preferred embodiment, the method is for diagnosing or monitoring the progression of a cancerous disease.

The nature of the method will depend on whether a peptide, nucleic acid or agent of the present invention is being detected (and if it is an agent, on the nature of that agent).

In order to detect a peptide of the present invention, an agent of the present invention (such as an antibody or an MHC molecule) may be used. Methods of screening with antibodies (such as ELISAs, immunoblotting, western blotting, competitive assays, two site capture assays) are well known in the art.

In order to detect peptides or specific T cells, an antigen presentation assay may be used. When a T cell successfully recognises an MHC:peptide complex, it is stimulated. This stimulation can be monitored by proliferation of the T cells (for example by incorporation of $^3$H) and/or by production of cytokines by the T cells (for example by an ELISPOT™ (ELISA) assay). Thus it is possible to detect the presence of a specific peptide by using appropriate APCs and T cells lines, and to detect the presence of a specific T cell by using appropriate APCs and peptide/antigen.

The presence of a particular cell surface molecule (such as a TCR or MHC molecule) can also be investigated using fluorescence activated cell scanning (FACS).

Where the method is to detect the presence of a nucleic acid, numerous methods are known in the art such as PCR, southern blotting (for DNA) and northern blotting (for RNA).

T Cells

The present invention also relates to a T cell, such as a T cell clone, or line, which is capable of specifically recognising a peptide epitope according to the present invention in conjunction with an MHC molecule. Several methods for generating T cell lines and clones are known in the art. One method for generating T cell lines is as follows:

Mice are primed with antigen (usually subcutaneously in the rear footpad), and the draining lymph nodes (in this case the popliteal and inguinal) are removed 1 week later and set up in co-culture with the antigen and with syngeneic feeder cells i.e. cells from mice of the same inbred line (e.g. normal thymocytes or splenocytes). After 4 days the lymphoblasts are isolated and induced to proliferate with IL-2. When the population of cells has expanded sufficiently, they are checked for antigen and MHC specificity in a lymphocyte transformation test, and are maintained by alternate cycles of culture on antigen-treated feeder cells and culture in IL-2-containing medium.

The definitive T-cell lineage marker is the T-cell receptor (TCR). There are presently two defined types of TCR, both of which are heterodimers of two disulphide-linked polypeptides. One type consist of $\alpha$ and $\beta$ chains, the other type consists of $\gamma$ and $\delta$ chains. Approximately 90-95% of blood T cells express $\alpha/\beta$ TCR, the other 5-10% expressing $\gamma/\delta$ TCR.

T cells can be divided into two distinct populations: a subset which carries the CD4 marker and mainly "helps" or "induces" immune responses ($T_H$) and a subset which carries the CD8 marker and is predominantly cytotoxic ($T_C$). CD4+ T cells recognise peptides in association with MHC class II molecules, whereas CD8+ T cells recognise peptides in association with Class I molecules, so the presence of CD4 or CD8 restricts the types of cell with which the T cell can interact.

The CD4 set has been functionally sub-divided into two further subsets:
  (i) T cells that positively influence the response of T cells and B cells (the helper T cell function) are CD29+. Practically all the cells in this population also express a low molecular weight isoform of the CD45 leucocyte common antigen, designated CD45RO.
  (ii) Cells that induce the supressor/cytotoxic functions of CD8+ cells (the suppressor/inducer function) express a different form of the CD45 molecule, CD45RA.

Functional diversity has also been demonstrated by functional analysis of $T_H$ clones for cytokine secretion patterns. The $T_H1$ subset of CD4+ T cells secrete IL-2 and IFN-$\gamma$, whereas the $T_H2$ subset produces IL-4, IL-5, IL-6 and IL-10. $T_H1$ cells mediate several functions associated with cytotoxicity and local inflammatory reactions. Consequently these cells are important for combating intracellular pathogens, including viruses, bacteria and parasites. $T_H^2$ cells are more effective at stimulating B cells to proliferate and produce antibodies, and therefore in normal immune responses function to protect against free-living organisms.

Expression of all of the markers described above can readily be detected using specific antibodies, so the type of T cell can be selected/determined using FACS. Expression of particular cytokines can also be detected by methods known in the art, such as ELISPOT™ (ELISA) assay.

Prophylactic/Therapeutic Methods

The present invention also provides the use of a vaccine according to the present invention in the manufacture of a medicament for use in the prevention and/or treatment of a disease.

There is also provided a method for treating and/or preventing a disease in a subject which comprises the step of administering an effective amount of a vaccine according to the present invention.

Administration of the vaccine may elicit an immune response in the subject. In a preferred embodiment, administration of the vaccine breaks immune tolerance to 5T4 in the subject.

Where the peptide is a class I epitope, the immune response elicited may involve the activation of 5T4 specific cytotoxic T-lymphocytes. Where the peptide is a class II epitope, the immune response elicited may involve the activation of $T_H1$ and/or $T_H2$ cells.

Advantageously, the response is an anti-tumour immunotherapeutic response which is effective to inhibit, arrest or reverse the development of a tumour in a subject.

Combination Therapies

The invention further relates to the use of 5T4 targeting molecules, such as anti-5T4 antibodies, for example anti-5T4 scFvs. These antibodies may be used to (i) to target natural or exogenous 5T4 in situ and/or (ii) deliver immune enhancer molecules, such as B7.1, to natural or exogenous 5T4 in situ (Carroll et al. (1998) J Natl Cancer Inst 90(24):1881-7). This potentiates the immunogenicity of 5T4 in the subject.

The present invention thus also relates to the sequential use of a vaccine according to the present invention and anti-5T4 antibodies, for example anti-5T4 scFvs. The anti-5T4 scFvs antibodies may be administered as naked DNA encoding the antibodies (for example, in a plasmid comprising the encoding DNA together with a short promoter region to control its production), in an expression vector (which may be viral or non-viral) comprising the encoding sequence or in a protein form. Thus, the invention provides a vector encoding a 5T4 peptide antigen and an agent capable of binding 5T4 which is optionally fused with an immunostimulatory molecule, for separate, such as sequential use, in the treatment of tumours.

In a further embodiment, the invention encompasses a combination therapy including enzyme/prodrug therapy and immunotherapy with 5T4. For example, the enzyme/prodrug therapy may comprise intratumoural or systemic delivery of P450, delivered optionally using an retroviral or lentiviral vector, and cyclophosphamide (CPA) followed by systemic immunotherapeutic induction with 5T4.

Thus, the invention further relates to a vector encoding 5T4 peptide antigen and a prodrug/enzyme combination, for separate, simultaneous separate or combined use in the treatment of tumours.

Diseases

5T4 is a tumour associated antigen. Presence of 5T4 on cancer cells is associated with metastasis and has been shown to be an independent indicator of prognosis in a number of different cancers.

In a preferred embodiment, the disease (which is preventable/treatable using a vaccine according to the present invention) is a cancer. In particular the disease may be a carcinoma of, for example, the breast, lung, stomach, pancreas, endometrium, cervix, colorectal, renal or prostate.

WO89/07947 describes an immunohistochemical screen of neoplastic tissues using an anti-5T4 monoclonal antibody (see Tables II and VI). Preferably, the disease is a cancer which can be shown to be 5T4 positive by diagnostic testing (such as with an anti-5T4 antibody), for example: an invasive carcinoma of the Ampulla of Vater, breast, colon, endometrium, pancreas, or stomach; a squamous carcinoma of the bladder, cervix, lung or oesophagus; a tubulovillous adenoma of the colon; a malignant mixed Mullerian tumour of the endometirem; a clear cell carcinoma of the kidney; a lung cancer (large cell undifferentiated, giant cell carcinoma, broncho-alveolar carcinoma, metastatic leiomyosarcoma); an ovarian cancer (a Brenner tumour, cystadenocarcinoma, solid teratoma); a cancer of the testis (seminoma, mature cystic teratoma); a soft tissue fibrosarcoma,; a teratoina (anaplastic germ cell tumours); or a trophoblast cancer (choriocarcimoma (e.g. in uterus, lung or brain), tumour of placental site, hydatidiform mole).

Tetramers

The present invention also provides 5T4 peptide epitope associated with (eg. folded with) tetramers and uses thereof.

Tetramers are fluorescent reagents that allow for the direct visualisation of antigen-specific T-cells (Altman et al. (1996) Science 271, 94-96). They consist of individual peptides epitopes refolded with HLA class I protein and bind to T cells that are specific for that particular epitope. They allow for the direct quantification of antigen specific lymphocytes and have been applied widely in human and murine immunology.

The tetramers may be prepared using the methods described by Altman et al. (1996) Science 271, 94-96. Briefly, tetramers may be prepared by adding biotinylated protein to streptavidin PE at a ratio of 4:1. Tetramer bound cells may be selected using magnetic activated cell sorting (MACS). MACS has been described in Radbruch et al. (1994) Methods in Cell Biology 42, 387-403.

Advantageously, the use of tetramers allows for the tracking of a 5T4-specific immune response before, during and after vaccination; to purify autologous CD4+ T cells from individual patients and expand/manipulate them ex vivo for possible re-infusion; as a diagnostic indicator, for example, in subjects prone to colorectal and other 5T4-positive cancers. Accordingly, the present invention also relates to the use of a ST4 peptide epitope tetramer for monitoring a 5T4-specific immune response before, during or after vaccination. The present invention further relates to the use of a 5T4 peptide epitope tetramer for the purification of autologous CD4+ T cells from individual patients. The present invention still further relates to the use of a 5T4 peptide epitope tetramer as a diagnostic indicator in subjects prone to 5T4-positive cancers—such as colorectal cancers.

BRIEF DESCRIPTION OF THE DRAWINGS

The invention is further described, for the purposes of illustration only, in the following examples in which reference is made to the following Figures.

FIG. 5 shows IFN gamma production by OB8 T cell clones.

EXAMPLES

5T4-specific immune response in healthy donors.

HST4 is a surface glycoprotein which is expressed on trophoblasts during gestation period but it is not present on normal adult tissues, with only weak expression on some specialised epithelia. By contrast, it is expressed by many human carcinomas. Its function is unknown but there is significant correlation between 5T4 expression and poor clinical prognosis. There is some evidence that primary 5T4-negative tumours give rise to 5T4-positive metastases.

Due to the fact that 5T4 is a self-protein, one may suspect that T cells specific for this protein should be eliminated during thymic development. However, there is evidence that low frequency low affinity 5T4-specific T cells exist in some people. Extensive studies on melanoma have shown that T cells reactive against self tissue-specific gene products can be detected in both melanoma patients and healthy individuals.

On the basis that the same may be true for the 5T4 antigen, the present inventors have undertaken random screening of healthy donors for the presence of 5T4-specific T cells ex vivo.

Example 1

Screening of a 5T4 Peptide Library

A 5T4 peptide library spanning the entire 5T4 protein and consisting of 10-mer peptides overlapping by 8 amino acids, was used in an ELISPOT™ (ELISA) assay.

ELISPOT™ (ELISA) assay was performed as described elsewhere (Czerkinsky et al (1988) in "Theoretical and Technical Aspects of ELISA and Other Solid Phase Immunoassays (D.M.Kemeny and SJ. Challacombe, eds.) pp217-239 John Wiley & Sons, New York). Briefly, PBMCs were separated by Histopaque-1077 and plated out at concentration of $5 \times 10^5$ cells per well of PVDF 96-well plate covered with interferon-capturing antibody. Pools often peptides were added to each well at final concentration of 20 ug/ml. Wells with DMSO and PHA served as negative and positive controls respectively. Also Influenza peptide was included as positive control. After O/N incubation a plate was washed with PBS-Tween and second-step antibody were added. The number of spots was counted by dissection microscope.

Figure 1:
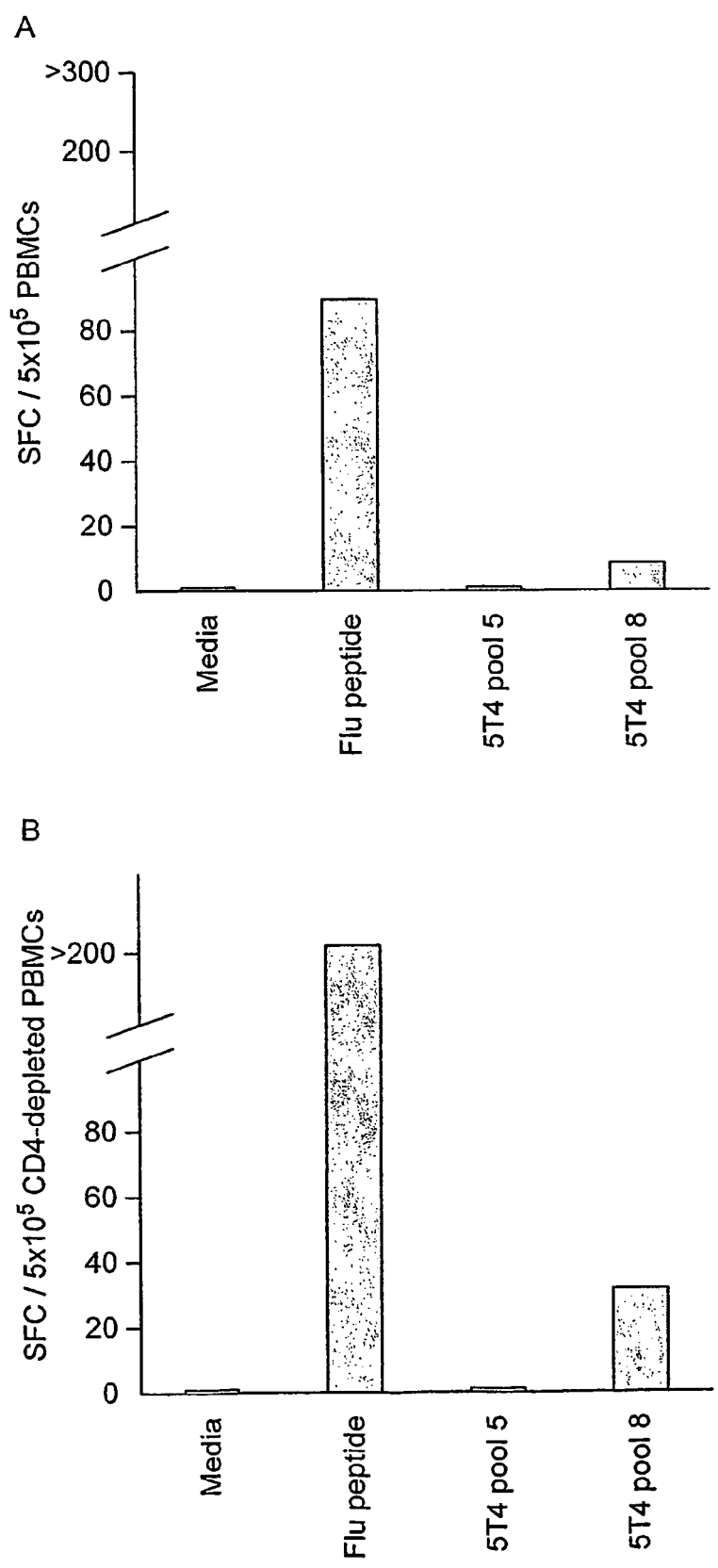
FIG. 1 shows an ELISPOT™ (ELISA) assay which reveals the presence of T cells specific for one of 5T4 peptide pools in the PBMCs from healthy donor ex vivo.
A. whole PBMCs
B. CD4 depleted PBMCs

Out of 20 healthy blood donors tested against 5T4 peptide library one donor, OB8, had a positive response to the peptide pool #8. PBMCs exposed to 5T4 peptide pool 8 produced 5 spots per $5 \times 10^5$ cells compared to no spots in response to any other peptide pools (FIG. 1A). Response to a Flu peptide was used as a positive control. CD4 depletion of PBMCs prior to ELISPOT™ (ELISA) assay significantly amplified the response (37 spots per $5 \times 10^5$ PBMCs) which led to the conclusion that IFN-gamma production was mediated by CD8+T cells. (FIG.1B).

Figure 2:
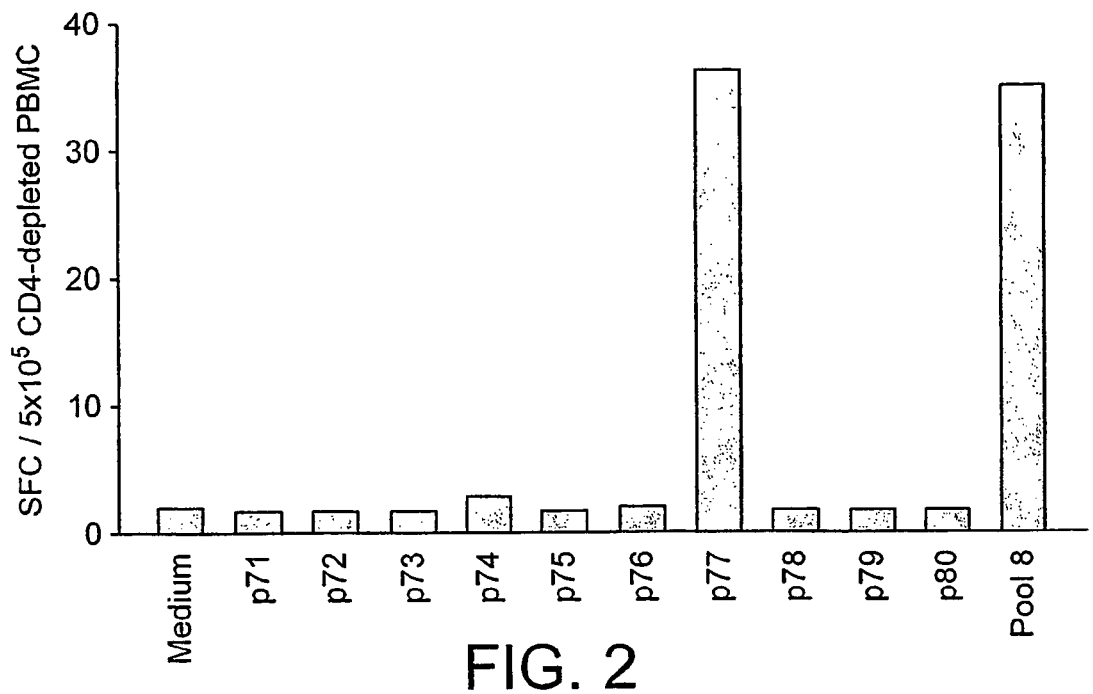
FIG. 2 shows an ELISPOT™ (ELISA) screen of the peptides constituting pool 8 to investigate which one(s) is responsible for inducing IFN gamma secretion.

Peptide pool #8 was pulled apart and each individual peptide was tested by ELISPOT™ (ELISA) assay in a similar way, using whole PBMC and CD4-depleted PBMC from donor OB8, which allowed us to identify a single epitope-peptide within 5T4 which was responsible for inducing secretion of IFNγ-p77, PLADLSPFAF, SEQ ID NO: 12 (FIG. 2).

Example 2

Testing the 5T4 Specificity of OB8 T Cells

To further characterize identified the epitope, an EBV-transformed B-cell line was established from this donor. The HLA class I type of donor OB8 was identified as HLA A 1,2 B 8,44 C 5,7.

Figure 3:
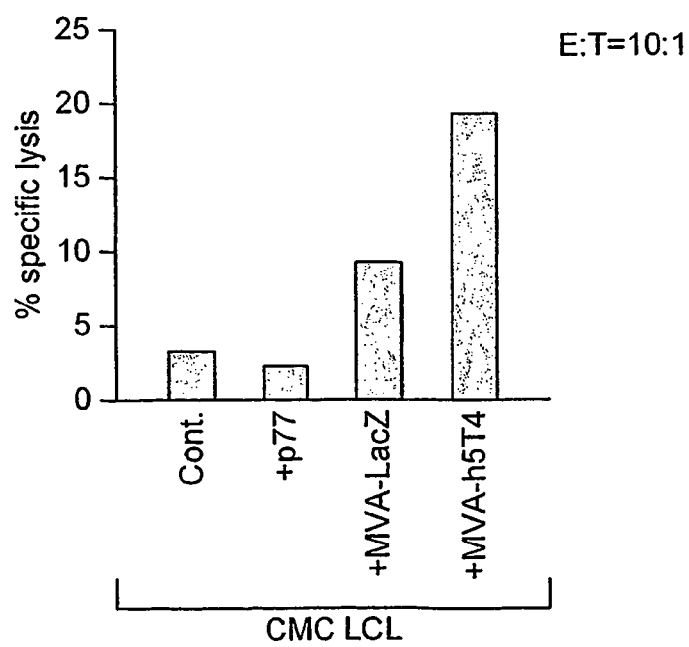
FIG. 3 shows a $^{51}$Cr-release assay showing that expanded 5T4-specific OB8 T cells recognise allogeneic CMC LCL target cells expressing 5T4 endogenously from MVA vector.

Peptide 77-specific T cells were expanded in vitro by co-culturing PBMC from OB8 with autologous DC pulsed with p77. After 3 weekly stimulations with autologous D C+p77 resulting polyclonal T cell line was tested for the presence of specific reactivity by CTL assay (FIG. 3). OB8 T cells recognized HLA-matched CMC LCL expressing the whole 5T4 antigen from an MVA vector over the background killing of MVA-LacZ-infected targets.

Figure 4:
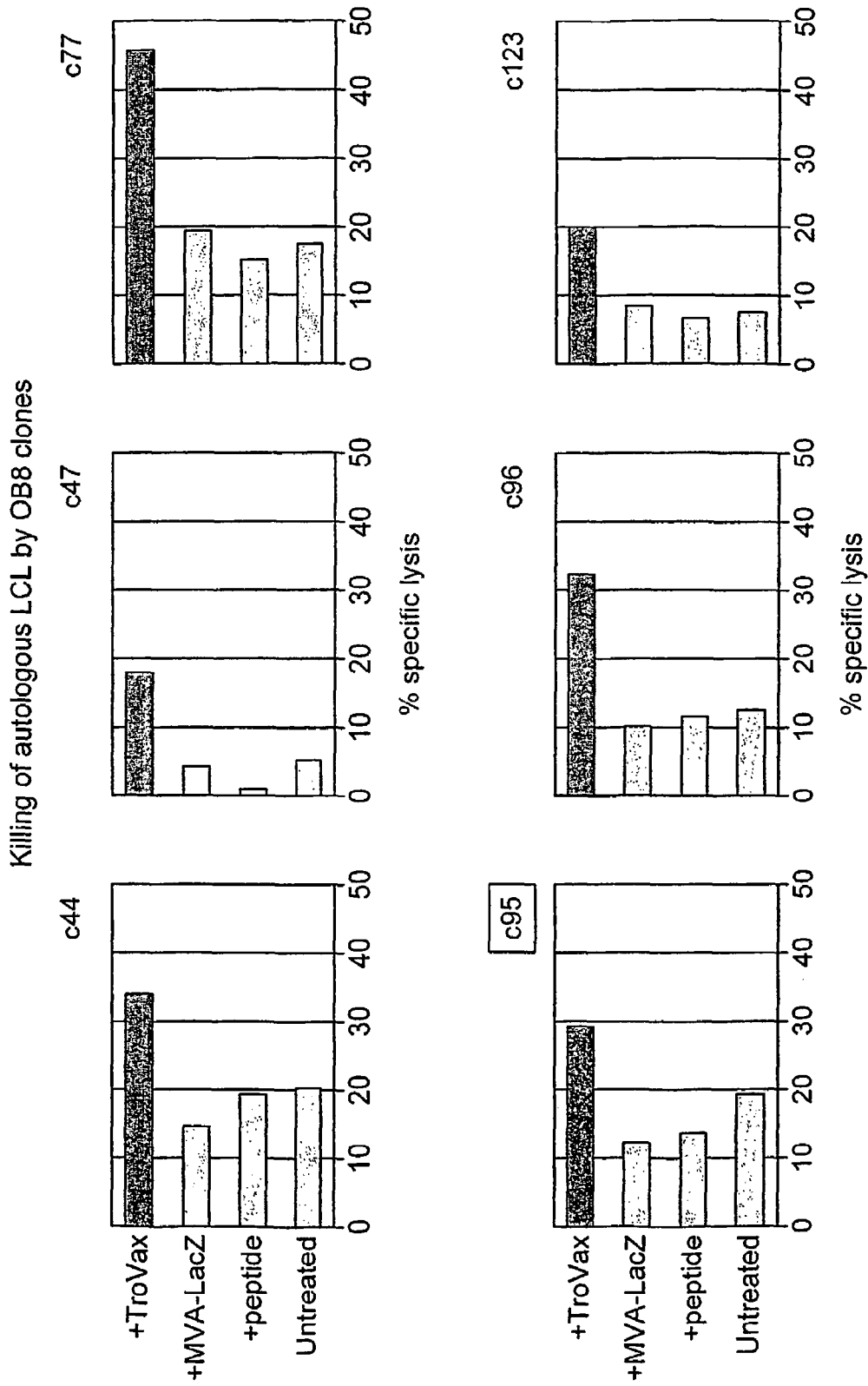
FIG. 4 shows that individual OB8 T cell clones isolated by limiting dilution are also 5T4 specific when tested by $^{51}$Cr-release assay.

By cloning by limiting dilution T cell clones were generated from polyclonal T cell line using p77-pulsed autologous LCL. The clones were expanded to growth in 2ml wells and then tested for specific reactivity by $^{51}$Cr-release assay. Autologous LCL, untreated, pulsed with p77, infected with TroVax and control vector were used as targets. About 35% of clones tested were specific for the whole antigen endogenously expressed in LCL from MVA vector. Representative results of a CTL assay are shown in FIG. 4.

Both cytolytic and non-cytolytic clones were tested for IFN-gamma production by ELISPOT™ (ELISA) assay. Some of the non-cytolytic clones produced IFN-gamma in response to stimulation with LCL loaded with p77 and infected with TroVax. The level of IFN production is expressed in relative units compared to background (FIG. 5).

Example 3

Identification of the HLA Restriction Element for the p77 Epitope

The next step was to identify an HLA restriction element of an epitope-peptide. LCLs which matched at one or two HLA alleles loaded with p77 were used as APCs in ELISPOT™ (ELISA) assay. This is a panel of LCLs used as APCs:

CMC—HLA A2,11 B8,44 C5,7
CD—HLA A1 B7,57, C6,7
IM17—HLA A1,2 B13,44 C5, 6
IM 108—HLA A3,11 B8,35 C4,7
IM 119—HLA A2,68 B15,40 C3

LCLs IM17 and IM119 loaded with p77 did not induce IFN-gamma production by OB8 CTLs which rules out HLA A1, A2, B44 and C5 alleles as restriction elements for the epitope. The strength of the response induced by other LCLs can be characterized as following:

Auto LCL>CMC LCL>IM108 LCL>CD LCL

| LCL + p77 | No. of spots per 1000 cells |
|---|---|
| Auto | >100 |
| CMC | 15.3 |
| IM 108 | 12 |
| CD | 3.7 |

The fact that p77 induced a response from strong to medium when autologous and two B8-matched LCLs were used as APCs leads to a conclusion the epitope is likely to be presented through B8 allele. However, there is a possibility that this peptide may also be presented by Cw7 allele also, because of the fact that CD LCL matched at Cw7 induce weak response as well.

Example 4

Identification of the Minimal Epitope

Figure 6:
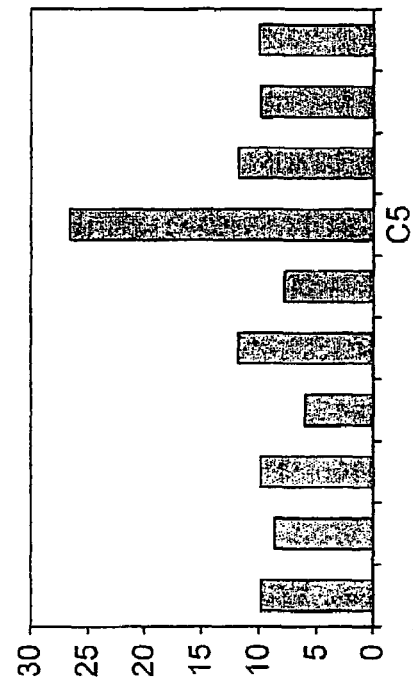
FIG. 6 shows a screen of p77 derivatives (peptides c1 through c8 as represented by SEQ ID NOs: 9, 10, 11, 12, 3, 13, 14 and 15, respectively) to identify the minimal epitope of P77.

In order to minimise HLA B8-restricted 5T4 epitope the peptides were synthesized which presented shorter or longer version of original p77. A number of clones were tested by CTL assay against LCL loaded with individual peptide in a $^{51}$Cr-release assay. One of the clones tested recognised a 9-mer peptide but there was no killing of LCL loaded with any other peptide. This led to the conclusion that c5 corresponds to the minimal epitope (FIG. 6).

Figures 7, 8:
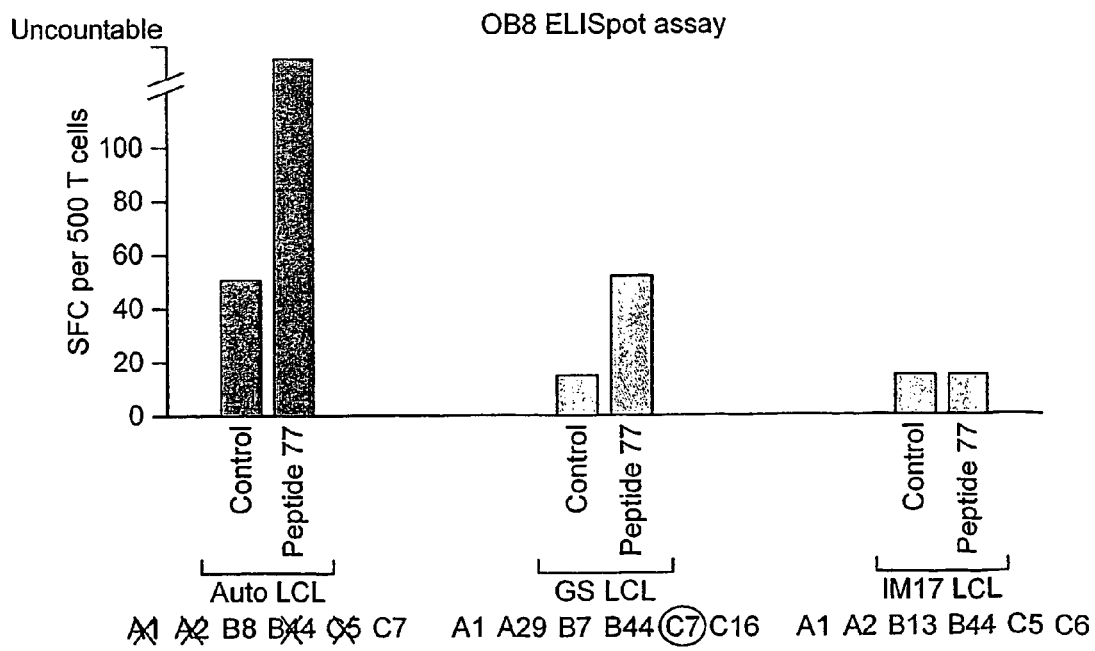
FIG. 7 shows an OB8 CTL assay
FIG. 8 shows an OB8 ELISPOT™ (ELISA) assay

The blood sample from the same donor was obtained 1 year later and polyclonal T cell line was generated de novo in a similar way using a defined minimal epitope peptide c5 to load DCs. After 4 weekly stimulations the growing cell population was tested by Cr-release and ELISPOT™ (ELISA) assays. As targets for Cr-release assay and APCs for ELISPOT™ (ELISA) assay the following LCLs were used: autologous LCL, IM 17 LCL (HLA A1,2 B13,44 C5,6) and GS LCL (HLA A2,29 B7,44, C7,16). CTLs strongly recognized autologous LCL loaded with c5 peptide reaching the level of killing of 70%. There was no recognition of IM17 targets pulsed with the peptide as was observed in a previous experiment. However, GS LCL loaded with c5 peptide were killed by OB8 CTLs but the levels of killing were lower (FIG. 7). The results of cytotoxicity assay correlated with ELISPOT™ (ELISA) assay data (FIG. 8).

Taken together, this leads to the conclusions that
either defined 5T4 epitope is presented by HLA B8 allele and cross-presented by Cw7 allele,
or it's presented by Cw7 allele only and in this case weaker recognition of Cw7-matched allogeneic LCL is due to the fact they are of different Cw7 subtype.

The Cw7 allele has not been characterized as extensively as others in regard to its primary anchor motifs. However, alanine in position 3 has been mentioned as one of those motifs (Marsh S, Parham P, Barber L The HLA Facts Book, Academic Press, 2000) which makes the Cw7 allele the most likely restriction element for the epitope.

This issue can be clarified by using cell lines expressing singular HLA allele, B8 or Cw7, as targets in Cr-release assay and/or APCs in ELISPOT™ (ELISA) assay.

Example 5

Stimulation of CD8+ Cells In Vitro by DCs Expressing 5T4

The present inventors have also demonstrated that dendritic cells (DCs), being professional APCs, can prime 5T4-specific IR in healthy donors in vitro. To this end, PBMCs from a HLA A2-positive healthy donor (HD123) were enriched for CD8+ T cells by negative selections. Autologous DCs, grown in the bags according to IDM technique, were infected with TroVax and added to respective CD8+ T cells to establish microcultures. After three-five rounds of weekly re-stimulations with TroVax-infected DCs resulting T cell microcultures were tested for the presence of 5T4-specific CTLs by Cr-release assay against autologous DC infected with recombinant adenovirus expressing 5T4 as target cells.

Figure 9:
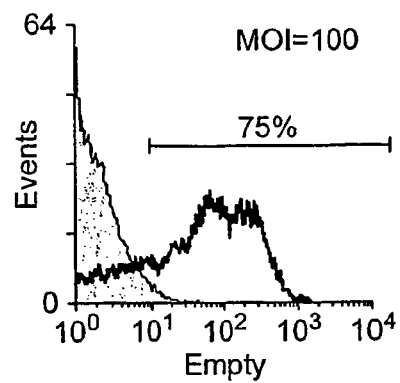
FIG. 9 shows FACS analysis of 5T4 expression in D Cs infected with recombinant Adenovirus encoding 5T4.

Expression of 5T4 from adenoviral vector in target cells was tested prior to conducting a CTL assay (FIG. 9). FACS analysis using an anti-5T4 antibody showed that 75% of DCs (infected with recombinant adenovirus encoding 5T4) expressed 5T4.

Figure 10:
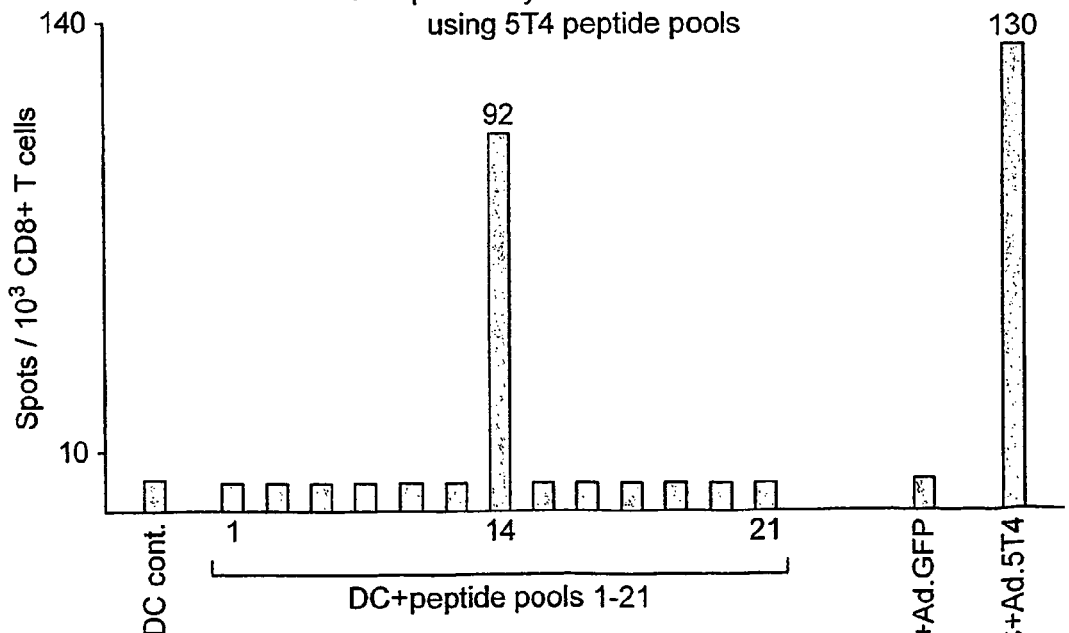
FIG. 10 shows an ELISPOT™ (ELISA) assay of T cell microculture using 5T4 peptide pools.

After 3 IVS some of the T cell microcultures showed weak (about 12-15%) 5T4-specific killing of autologous target cells. Those T cells were tested for IFN gamma production by ELISPOT™ (ELISA) assay. Autologous DCs expressing whole protein from adenoviral vector and loaded with 5T4 peptide pools as described above were used as stimulator cells. Some T cell microcultures were 5T4 positive, producing 130 spots per 103 cells in response to DC infected with Ad.5T4. These T cells were also positive to peptide pool 14 of 5T4 (92 spots per 103 cells). This the single peptide pool #14 was identified as being the one which induced IFN gamma secretion by T cells (FIG. 10).

Figures 11, 12:
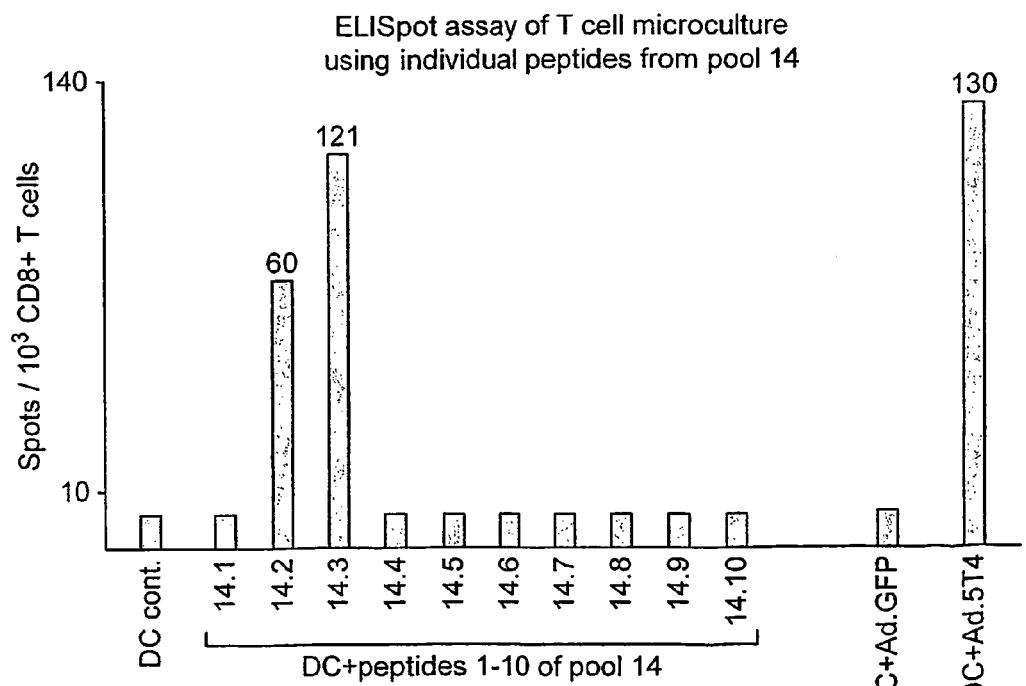
FIG. 11 shows the amino acid sequences 14.2 (SEQ ID NO:4) and 14.3 (SEQ ID NO:5) peptides.
FIG. 12 shows an ELISPOT™ (ELISA) assay of T cell microculture using individual peptides from pool 14.

An ELISPOT™ (ELISA) assay was repeated after 4 IVS with the similar result. The individual 10-mer peptides constituting pool 14 were included into this assay which identified two adjacent peptides as inducing positive response—p14.2 and p14.3 (FIG. 11), although the response induced by p14.3 was significantly stronger (FIG. 12). Two more T cell microcultures were tested by ELISPOT™ (ELISA) in a similar way and one out of two microcultures appeared to be 5T4-specific with the same p14.3 inducing IFN gamma production. Taken together these data lead to suggestion that p14.3 is a naturally processed CD8 T cell epitope within 5T4 antigen.

Figures 13, 14:
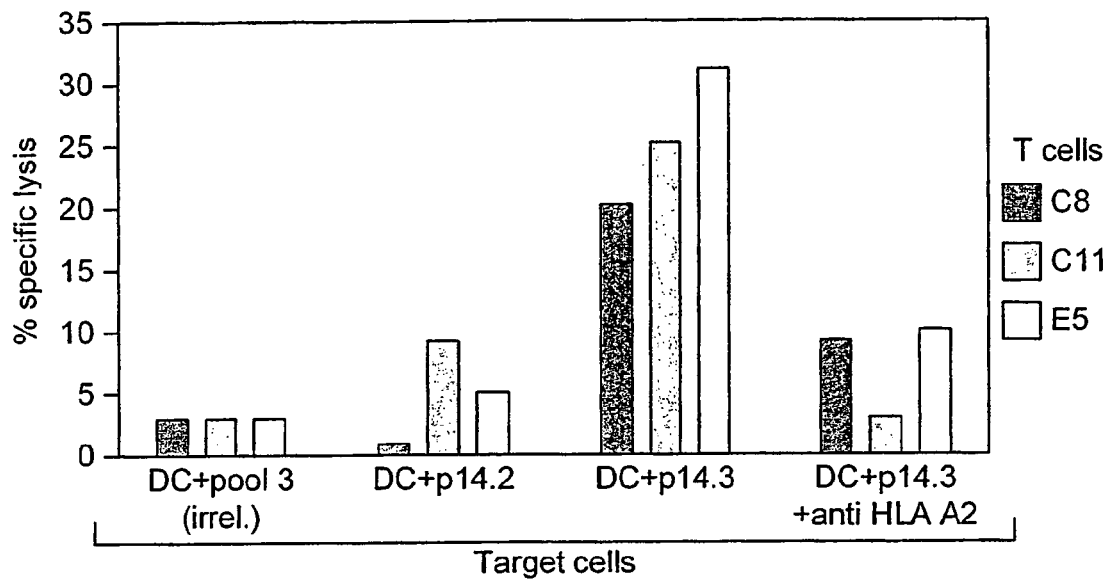
FIG. 13 shows blocking of target cell recognition with anti-HLA A2 antibodies in $^{51}$Cr-release assay.
FIG. 14 shows the amino acid sequence of shorter versions of 14.3 and 14.2 peptides (represented by SEQ ID NOS: 6, 7 and 8, respectively).

To test the possibility of HLA A2 allele being restricting element for identified epitope the present inventors performed Cr-release assay using, as target cells, autologous DCs pretreated with anti HLA A2 antibody prior to peptide sensitization with p14.3. In more detail, three T cell microcultures C8, C11 and E5 were tested against peptides 14.2 and 14.3-pulsed targets by 51Cr-release assay. Peptide 14.3 was recognised by all three T cell microcultures and only C11 T cells killed p14.2-loaded targets at low level. When Dcs were pretreated with anti-HLA A2 Abs prior to pulsing with p14.3, their recognition by T cells was abrogated. These results demonstrate that p14.3 is indeed presented by HLA A2 allele. (FIG. 13).

Figure 15:
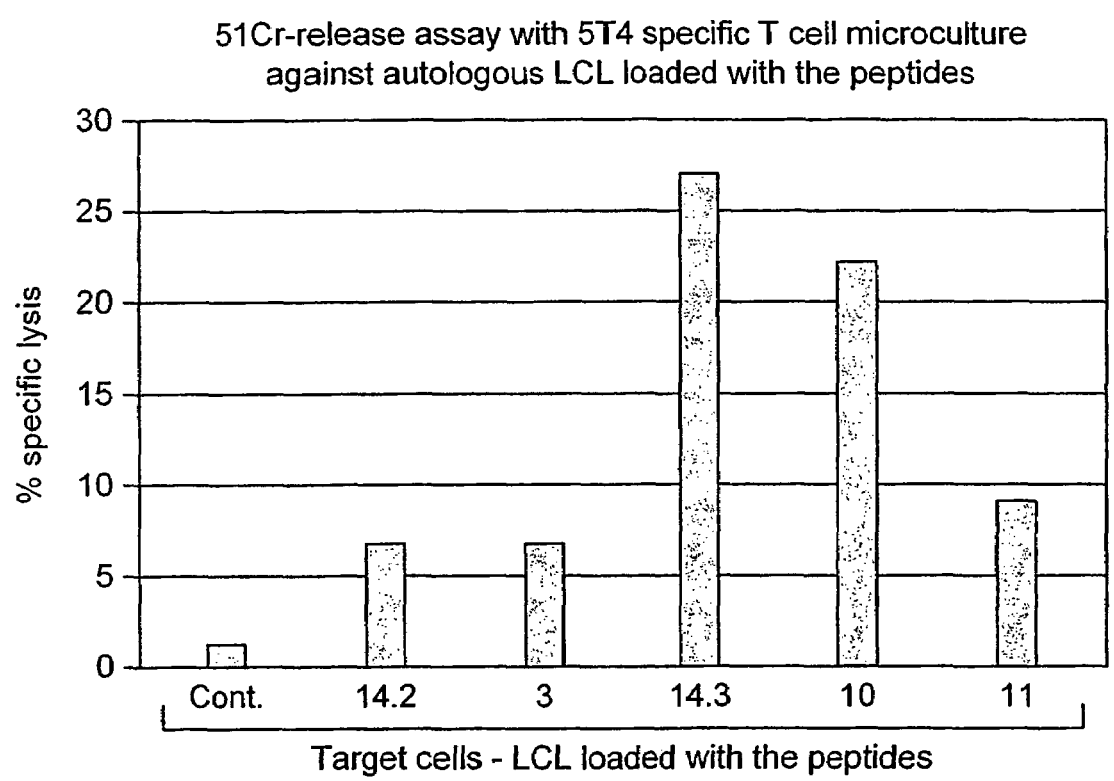
FIG. 15 shows the 51Cr-release assay with 5T4 specific T cell microculture against autologous LCL loaded with the peptides

Blood sample from the same donor was obtained 6 months later. To confirm that the 5T4-specific response is a primary response, CD8+ T cells were separated into naïve and memory T cells on the basis of CD45RA expression. T cells microcultures were set up from total CD8+ T cells, CD8+ CD45RA+ and CD8+CD45RA- T cells. After 5 rounds of weekly stimulation with TroVax-infected DCs T cell microcultures were tested by the 51 Cr -release assay as described above. None of the T cell microcultures generated from CD45RA -cells were cytotoxic, whereas both total CD8+ T cells and CD45RA+CD8+ T cells produced 5T4-specific populations which proves that 5T4-specific immune response was primed in vitro. These T cell cultures were used to identify a minimal epitope within a 10-mer peptide as had been done for donor OB8. 51Cr-release assay was performed using autologous LCL loaded with 14.3 and 14.2 peptides, including in the assay three other peptides representing shorter versions of 14.3 and 14.2 (FIG. 14). According to the binding prediction algorithms 9-mer peptide #3 is the strongest candidate for an HLA A2-restricted minimal epitope, having Leucine in position 2 and Valine in position 9 as primary anchor residues. However, in contrast to our expectations, original peptide 14.3 induced the strongest response (FIG. 15). These data were corroborated by ELISPOT™ (ELISA) assay (data not shown). Based on these data, we conclude that a10-mer peptide 14.3 is a natural A2-restricted epitope within 5T4 antigen. To support this, HLA A2 tetramer complexed with 14.3 peptide has been made despite the fact that generally Glutamic acid in position 2 has a negative effect on peptide folding within MHC grove and the success of making such a tetramer is usually poor.

In the course of monitoring an immune response in colorectal cancer patients by ex vivo ELISPOT™ (ELISA) assay we have detected a response to pool 8 containing the earlier described peptide 77 in a patient whose HLA type included Cw7 allele. Two other patients (HLA type unknown) have demonstrated a response to peptide pool 10.

A patient with HLA type A2, 11 B7,27, Cw2,7 has responded to pool 11. Pool 11 contains a number of peptides that according to binding prediction algorithms are among the strongest binders to HLA Al and B27 alleles. For instance, peptide 11.2 has got a top score among 5T4 10-mer peptides binding to HLA A2 allele; peptide 11.4 is the 7$^{th}$ from the top among A2-binders. Peptide 11.7 has got a top score among 5T4 10-mer peptides binding to HLA B27 allele; peptide 11.3 is the 2nd and 11.4 is the 5h from the top among B27-binders. All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A nucleic acid molecule encoding an MHC class I peptide epitope of 5T4 comprising the amino acid sequence of SEQ ID NO: 3.

2. A vector comprising the nucleic acid molecule of claim 1.

* * * * *